(12) United States Patent
Landis et al.

(10) Patent No.: US 7,737,272 B2
(45) Date of Patent: Jun. 15, 2010

(54) DIAZAPHOSPHACYCLE TRANSITION METAL COMPLEXES

(75) Inventors: Clark R. Landis, Madison, WI (US); Wiechang Jin, Madison, WI (US); Jonathan S. Owen, Pasadena, CA (US); Thomas P. Clark, Madison, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 22 days.

(21) Appl. No.: 12/032,350

(22) Filed: Feb. 15, 2008

(65) Prior Publication Data

US 2008/0146798 A1  Jun. 19, 2008

Related U.S. Application Data

(62) Division of application No. 10/787,554, filed on Feb. 26, 2004, now Pat. No. 7,355,072, which is a division of application No. 09/911,367, filed on Jul. 23, 2001, now Pat. No. 7,071,357.

(51) Int. Cl.

| | |
|---|---|
| C07D 487/00 | (2006.01) |
| C07D 243/00 | (2006.01) |
| C07D 255/00 | (2006.01) |
| C07D 257/00 | (2006.01) |
| C07D 259/00 | (2006.01) |
| C07D 487/22 | (2006.01) |
| C07D 491/00 | (2006.01) |
| C07D 498/00 | (2006.01) |
| C07D 237/26 | (2006.01) |
| C07D 237/28 | (2006.01) |
| C07D 237/36 | (2006.01) |
| C07D 293/00 | (2006.01) |
| C07D 421/00 | (2006.01) |
| C07D 517/00 | (2006.01) |
| C07F 3/12 | (2006.01) |

(52) U.S. Cl. .................. 540/471; 540/553; 540/554; 540/555; 544/233; 544/234; 544/235; 544/236; 548/100; 548/108

(58) Field of Classification Search .................. None
See application file for complete search history.

(56) References Cited

U.S. PATENT DOCUMENTS

| 7,355,072 B2 | 4/2008 | Landis et al. |
| 7,355,073 B2 | 4/2008 | Landis et al. |
| 2003/0055254 A1 | 3/2003 | Landis et al. |

FOREIGN PATENT DOCUMENTS

| WO | WO 91/17988 | 11/1991 |
| WO | WO 03/010174 | 2/2003 |

OTHER PUBLICATIONS

Ertl. Journal of Chemical Information and Computational Sciences, 2003, 43, 374-80.*

Fey et al. Organometallics, 2008, 27 (No. 7), 1372-83.*
Märkl, G., et al., "1.5-Diaza-3-Phospha-Cycloheptane N.N'-Bis-[Phosphinomethyl]-Ehtylendiamine Mit Optisch Aktiven Seitenketten," Tetrahedron Letters, vol. 21, pp. 3467-3470 (1980), published by Pergamon Press Ltd., Oxford, Great Britain.
Märkl, G., et al., "1.2-Diaza-4-Phospha-Cyclopentane—1.5-Diaza-3.7-Diphospha-Bicyclo-[3.3.0] Octane N.N'-[Bisphosphinomethylen]-N.N'-Dimethylhydrazine 1.3-Diaza-5-Phospha-Cyclohexane," Tetrahedron Letters, vol. 22, pp. 229-232 (1981), published by Pergamon Press Ltd., Oxford, Great Britain.
Arbuzov, B.A., et al., "Synthesis and Structure of 1,5-Diaza-3,7-Diphosphacyclooctanes," Bulletin of Academy of Science of USSR, Division of Chemical Science, pp. 1672-1676 (1984), published by Plenum Publishing Corp., New York, New York translated from Izvestiya Akademii Nauk SSSR, Seriya Khimicheskaya, No. 8, pp. 1846-1850, Aug. 1983.
Alcock, N., et al., "Substrate-induced Kinetic Resolution of Racemic Biphosphines in situ for Homogeneous Catalysis," J. Chem. Soc. Chem. Commun., pp. 1532-1534 (1986), published by Royal Chemical Society, London, England.
Burk, M. J., et al., "New Electron-Rich Chiral Phosphines for Asymmetric Catalysis," Organometallics, vol. 9, pp. 2653-2655 (1990), published by the American Chemical Society, Washington, D.C.
Burk, M. J., et al., "$C_2$-Symmetric Bis(phospholanes) and Their use in Highly Enantioselective Hydrogenation Reactions," J. Am. Chem. Soc., vol. 113, pp. 8518-8519 (1991), published by American Chemical Society, Washington, D.C.
Faller, J. W., et al., "Chiral Poisoning: A Novel Strategy for Asymmetric Catalysis," J. Am. Chem. Soc., vol. 115, pp. 804-805 (1993), published by American Chemical Society, Washington, D.C.
Khairullin, V. K., et al., "Reaction of N,N'-Dibenzylidenehydrazine with Dialkyl Hydrogen Phosphites and Phosphinic and Thioglycolic Acids," Russian Journal of General Chemistry, vol. 64, No. 4, pp. 557-559 (1994), published by Plenium Publishing Corp., New York, New York.
Kacker, S., et al., "Alternating Copolymers of Functional Alkenes with Carbon Monoxide," Macromolecules, vol. 29, pp. 5852-5858 (1996), published by American Chemical Society, Washington, D.C.
Jandeleit, B., et al., "Combinatorial Materials Science and Catalysis," Angew. Chem. Int. Ed., vol. 38, pp. 2495-2532 (1999), published by Wiley-VCH Verlag GmbH, Weinheim, Germany.
Portnoy, M., et al., "Solid-Phase Synthesis of an α-Aminophosphine Library," J. Comb. Chem., vol. 3, pp. 524-527 (2001), published by American Chemical Society, Washington, D.C.

(Continued)

Primary Examiner—James O Wilson
Assistant Examiner—Noble Jarrell
(74) Attorney, Agent, or Firm—Foley & Lardner LLP

(57) ABSTRACT

Transition metal complexes include a diazaphosphacycle of formula III and a transition metal. The phosphorus atom of the diazaphosphacycle is bonded to the transition metal and the diazaphosphacycle of formula III has the following structure

III

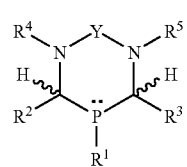

where the variables have the values set forth herein.

11 Claims, 11 Drawing Sheets

OTHER PUBLICATIONS

Wilhelm, H., et al., "Zur Reaktion Von Phosphoryl- Und Thiophosphorylisothiocyanaten Mit Phosphanen-Die Kristallstruktur Des $(C_6H_5O)_2P(O)$-NH-C(S)P$(C_6H_5)_2$," Phosphorus, Sulfur, and Silicon, vol. 73, pp. 81-91 (1992), published by Gordon Breach Science Publishers S. A., United States.

Ben-Arroya, B., et al., "Addition of borane-protected secondary phosphines to imines. A route to protected mono-N-substituted-α-aminophosphines," Tetrahedron Letters, vol. 41, pp. 6143-6147 (2000), published by Pergamon Press Ltd., Oxford, Great Britain.

Landis, C. R. et al., "Rapid Access to Diverse Arrays of Chiral 3,4-Diazaphospholanes," Angew. Chem. Int. Ed., vol. 40, pp. 3432-3434 (2001), published by Wiley-VCH Verlag GmbH, Weinheim, Germany.

Clark et al, "Highly Active, Regioselective, and Enantioselective Hydroformylation with Rh Catalysts Ligated by Bis-3,4-diazaphospholanes," *J. Am. Chem. Soc.*, 2005, 127, pp. 5040-5042; published by American Chemical Society.

Clark, T. P. et al., "Resolved Chiral 3,4-Diazaphospholanes and Their Application to Catalytic Asymmetric Allylic Alkylation," J. Am. Chem. Soc., vol. 125, pp. 11792-11793 (2003); published by American Chemical Society.

Landis, C. R. et al., "Solid-phase synthesis of chiral 3,4-diazaphospholanes and their application to catalytic asymmetric allylic alkylation," PNAS, vol. 101, No. 15, pp. 5428-5432 (2004).

* cited by examiner $^1$H NMR

DIAZAPHOSPHACYCLE TRANSITION METAL COMPLEXES

CROSS REFERENCES TO RELATED APPLICATIONS

This application is a division of U.S. patent application Ser. No. 10/787,554, filed Feb. 26, 2004, which is a division of U.S. Ser. No. 09/911,367, filed Jul. 23, 2001, now U.S. Pat. No. 7,071,357, the entire disclosures of which are hereby incorporated by reference in their entirety and for all purposes as if fully set forth herein.

GOVERNMENT RIGHTS

This invention was made with United States government support awarded by the following agency: DOE DE-FG02-99ER14949. The United States has certain rights in this invention.

FIELD OF THE INVENTION

The invention relates generally to diazaphosphacycles and to methods for synthesizing them. The invention also relates to metal complexes that may be formed from the novel diazaphosphacycles and to their use as catalysts.

BACKGROUND OF THE INVENTION

Phosphines are used as ligands in a large number of known transition metal complexes, and phosphine ligands are included in many transition metal complexes used as catalysts. One of the reasons is that phosphines are known to be one of the best ligands for stabilizing transition metals. Phosphine ligands are often included in transition metal complexes used to catalyze hydroformylation reactions where hydrogen, an alkene, and carbon monoxide are converted to the corresponding aldehyde.

Phosphines are also included as ligands in various transition metal complexes used to catalyze hydrogenation reactions. In many of these reactions, inexpensive phosphines such as triphenylphosphine perform suitably. However, phosphines have also found a niche in more specialized areas such asymmetric hydrogenation and other catalytic transformations. The use of a chiral phosphine allows enantioselectivity in the catalytic reaction, and often high enantiomeric excesses may be achieved when a chiral phosphine is used as a ligand. The use of an enantioselective catalyst allows a desired enantiomer to be produced reducing undesired products while simultaneously reducing separation costs associated with the separation of enantiomers. Enantioselective hydrogenation catalysts may be as fast and selective as some of the best known enzymes, and such catalysts can result in greater than 99.9% production of one enantiomer.

Asymmetric hydrogenation is used to make commercially important products including biologically active compounds such as pesticides and pharmaceuticals. Asymmetric hydrogenation is being used more frequently in the pharmaceutical industry where expensive intermediate compounds are too valuable to waste. One of the first reactions employing a phosphine-containing catalyst in the pharmaceutical industry was the selective production of L-DOPA rather than R-DOPA.

As noted above, chiral phosphine ligands are central to many developments in transition metal-catalyzed enantioselective transformations. R. Noyori, *Asymmetric Catalysis*; John Wiley: New York, 1994. Recent demonstrations of high enantioselectivity for a wide range of hydrogenation reactions with Rh complexes of the DuPHOS, PennPHOS, RoPHOS, BASPHOS, CnrPHOS, and related ligands highlight the unusual efficacy of rigid phosphacycles. M. J. Burk, J. Am. Chem. Soc. 1991, 113, 8518-8519; M. J. Burk, Chemtracts-Organic Chemistry 1998, 11, 787-802; M. J. Burk, A. Pizzano, J. A. Martin, L. M. Liable-Sands, A. L. Rheingold, Organometallics 2000, 19, 250-260; M. J. Burk, F. Bienewald, S. Challenger, A. Derrick, J. A. Ramsden, J. Org. Chem. 1999, 64, 3290-3298; Z. Zhang, G. Zhu, Q. Jiang, D. Xiao, X. Zhang, J. Org. Chem. 1999, 64, 1774-1775; Q. Jiang, Y. Jiang, D. Xiao, P. Cao, X. Zhang, Angew. Chem. 1998, 110, 1100-1103; Angew. Chem., Int. Ed. Engl 1998, 37, 1100-1103; G. Zhu, P. Cao, Q. Jiang, X. Zhang, J. Am. Chem. Soc. 1997, 119, 1799-1800; Z. Chen, Q. Jiang, G. Zhu, D. Xiao, P. Cao, C. Guo, X. Zhang, J. Org. Chem. 1997, 62, 4521-4523; J. Holz, M. Quirmbach, U. Schmidt, D. Heller, R. Stürmer, A. Börner, J. Org. Chem. 1998, 63, 8031-8034; W. Li, Z. Zhang, D. Xiao, X. Zhang, J. Org. Chem. 2000, 65, 3489-3496; W. Li, Z. Zhang, D. Xiao, X. Zhang, Tetrahedron Lett. 1999, 40, 6701-6704; Y.-Y. Yan, T. V. RajanBabu, J. Org. Chem. 2000, 65, 900-906; J. Holz, D. Heller, R. Stürmer, A. Börner, Tetrahedron Lett. 1999, 40, 7059-7062; A. Marinetti, S. Jus, J.-P. Genêt, Tetrahedron Lett. 1999, 40, 8365-8368; A. Marinetti, S. Jus, J.-P. Genêt, L. Ricard, Tetrahedron 2000, 56, 95-100; A. Marinetti, S. Jus, J.-P. Genêt, Tetrahedron Lett. 1999, 40, 8365-8368; A. Marinetti, S. Jus, J.-P. Genêt, L. Ricard, Tetrahedron 2000, 56, 95-100.

Although significant efforts have been made to produce transition metal complexes for effecting enantioselective catalytic transformations, one persisting problem associated with chiral phosphine ligands is that they are difficult and expensive to produce, often requiring multi-step syntheses. Both the electron density of the phosphorus atom in phosphines and the size of the phosphine ligand as expressed by cone angles are known to impact the reactivity of metal complexes prepared from them. Therefore, the ability to modify chiral phosphines and determine structure property relationships are important factors in understanding and optimizing catalytic activity. However, the difficulty associated with synthesizing chiral phosphines has prevented the synthesis of libraries of such compounds for use in analyzing structure property relationships.

One specific group of phosphines, 3,4-diazaphospholanes, are five-membered rings containing two nitrogen atoms, two carbon atoms, and a phosphorus atom as ring members. In 3,4-diazaphospholanes, each of the two carbon atom ring members is bonded to one of the ring nitrogen atoms and the ring phosphorus atom. Very few 3,4-diazaphospholanes have thus far been reported.

Märkl et al. have prepared diazaphospholanes by reacting hydrazines with phosphorus compounds having the formula $RP(CH_2OH)_2$. This synthetic methodology is limited and does not provide any simple route to compounds having groups other than H bonded to the diazaphospholane ring carbon atoms. G. Märkl, G. Y. Jin, Tetrahedron Lett. 1980, 21, 3467-3470; and G. Märkl, G. Y. Jin, Tetrahedron Lett. 1981, 22, 229-232. Arbuzov et al. have utilized the same type of methodology to prepare other diazaphosphacycles from $RP(CH_2OH)_2$. B. A. Arbuzov, O. A. Erastov, G. N. Nikonov, R. P. Arshinova, I. P. Romanova, R A. Kadyrov, Izvestia Akad, Nauk SSSR, Seriya Khimicheskaya, 1993, 8, 1846-1850.

A need remains for chiral phosphines and methods for making them. A need also remains for transition metal complexes that include chiral phosphines and for transition metal complexes for catalyzing important reactions. A need further remains for libraries of chiral phosphines and transition metal complexes.

SUMMARY OF THE INVENTION

The present invention provides diazaphosphacycles and methods for synthesizing them. The invention also provides transition metal complexes that include diazaphosphacycles and methods for using them in catalytic transformations.

A method of synthesizing a diazaphosphacycle is provided which includes reacting a phosphine with a diimine and optionally one or more equivalents of an acid halide, a sulfonyl halide, a phosphoryl halide, or an acid anhydride in the substantial absence of $O_2$ to form the diazaphosphacycle. The phosphine has the formula I

  I where $R^1$ is selected from the group consisting of substituted and unsubstituted aryl groups, substituted and unsubstituted alkyl groups, substituted and unsubstituted alkenyl groups, substituted and unsubstituted cycloalkyl groups, and substituted and unsubstituted ferrocenyl groups.

Methods for synthesizing diazaphosphacycles are also provided in which the diimine has the formula II and the diazaphosphacycle formed has the formula III

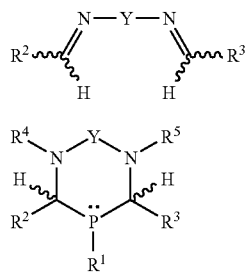

where:
$R^2$ and $R^3$ are independently selected from the group consisting of substituted and unsubstituted aryl groups, substituted and unsubstituted alkyl groups, substituted and unsubstituted cycloalkyl groups, substituted and unsubstituted heterocyclyl groups, and substituted and unsubstituted ferrocenyl groups;

$R^4$ is selected from the group consisting of —H, substituted and unsubstituted alkyl groups, substituted and unsubstituted cycloalkyl groups, substituted and unsubstituted aryl groups, trialkylsilyl groups, triarylsilyl groups, alkyldiarylsilyl groups, dialkylarylsilyl groups, —C(═O)—$R^6$ groups, —S(═O)$_2$—$R^6$ groups, —P(═O)$R^6R^7$ groups, and —C(═N$R^6$)—$R^7$ groups;

$R^5$ is selected from the group consisting of —H, substituted and unsubstituted alkyl groups, substituted and unsubstituted cycloalkyl groups, substituted and unsubstituted aryl groups, trialkylsilyl groups, triarylsilyl groups, alkyldiarylsilyl groups, dialkylarylsilyl groups, —C(═O)—$R^7$ groups, —S(═O)$_2$—$R^6$ groups, —P(═O)$R^6R^7$ groups, and —C(═N$R^6$)—$R^7$ groups;

$R^6$ is selected from the group consisting of substituted and unsubstituted alkyl groups, substituted and unsubstituted alkenyl groups, substituted and unsubstituted cycloalkyl groups, substituted and unsubstituted aryl groups, —OH groups, substituted and unsubstituted alkoxy groups, substituted and unsubstituted aryloxy groups, —NH(alkyl) groups, —NH(aryl) groups, —N(aryl)$_2$ groups, —N(alkyl)$_2$ groups, —N(alkyl)(aryl) groups, —S-alkyl groups, and S-aryl groups;

$R^7$ is selected from the group consisting of substituted and unsubstituted alkyl groups, substituted and unsubstituted alkenyl groups, substituted and unsubstituted cycloalkyl groups, substituted and unsubstituted aryl groups, —OH groups, substituted and unsubstituted alkoxy groups, substituted and unsubstituted aryloxy groups, —NH(alkyl) groups, —NH(aryl) groups, —N(aryl)$_2$ groups, —N(alkyl)$_2$ groups, —N(alkyl)(aryl) groups, —S-alkyl groups, and S-aryl groups;

$R^6$ and $R^7$ may be part of the same alkyl group, alkenyl group, or aryl group such that $R^4$ and $R^5$ together with the two nitrogen atoms of the diazaphosphacycle form a ring; and Y is a linking group selected from the group consisting of substituted and unsubstituted cycloalkyl groups, substituted and unsubstituted aryl groups, substituted and unsubstituted alkenyl groups, silyl groups, substituted alkyl groups, and groups having the formula —(CH$_2$)$_n$— wherein n is selected from the group consisting of 0, 1, 2, and 3.

Some methods are provided in which n is 0. Other methods are provided in which $R^2$ and $R^3$ are identical, but are not part of the same group. Still other methods are provided in which Y is a cycloalkyl group, wherein one of the N atoms of the diimine is bonded to a first ring member C atom of the cycloalkyl group and the other N atom of the diimine is bonded to a second ring member C atom that is bonded to the first ring member C atom. Yet other methods are provided in which Y has the formula

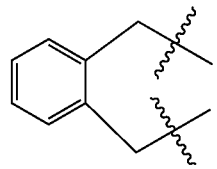

and the benzene ring of Y may be additionally substituted.

Methods are also provided in which the diazaphosphacycle is selected from compounds having the formula IIIA or IIIB or mixtures thereof

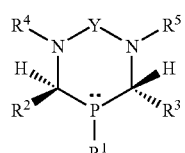  IIIA

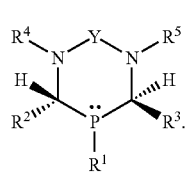  IIIB

Still other methods are provided in which the diazaphosphacycle has the formula IIIC

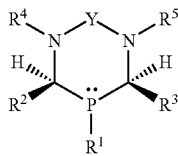

IIIC

Still other methods for synthesizing a diazaphosphacycle are provided in which the phosphine and the diimine are reacted in the presence of an acid such as hydrochloric acid or hydrobromic acid.

In still other provided methods for synthesizing a diazaphosphacycle, the phosphine and the diimine are reacted in the presence of the acid halide, the sulfonyl halide, the phosphoryl halide, or the acid anhydride, and at least one of $R^4$ and $R^5$ is not H. In still other such methods $R^4$ is a —C(=O)—$R^6$ group and $R^5$ is a —C(=O)—$R^7$ group. In still other methods in which the phosphine and the diimine are reacted in the presence of an acid halide, the acid halide is phthaloyl dichloride or phthaloyl dibromide.

Other methods for synthesizing a diazaphosphacycle are provided in which $R^1$ includes one or more —$PH_2$ group such that the phosphine is a polyphosphine. In still other such methods, the polyphosphine is selected from 1,2-diphosphinoethane, 1,2-diphosphinoethylene, 1,3-diphosphinopropane, substituted or unsubstituted 1,2-diphosphinobenzene groups, substituted or unsubstituted 1,8-diphosphinoanthracene groups, substituted or unsubstituted 1,8-diphosphino-9,10-dihydroanthracene groups, substituted or unsubstituted 1,8-diphosphinoxanthene groups, or 1,1'-diphosphinoferrocene groups.

Still other method for synthesizing diazaphosphacycles are provided in which the phosphine, the diimine, and optionally the acid halide are reacted in a substantially deoxygenated solvent such as ether, an alcohol, water, dichloroethane, or combinations of these.

Still further methods for synthesizing diazaphosphacycles are provided. These methods further include reacting an acid halide, an acid anhydride, a phosphoryl halide, or a sulfonyl halide with the diazaphosphacycle to produce a second diazaphosphacycle where $R^4$ and $R^5$ are both —H in the diazaphosphacycle and at least one of $R^4$ and $R^5$ is not —H in the second diazaphosphacycle.

In yet another provided method, the method is used to generate a library of different diazaphosphacycles such as by using a combinatorial method.

Another method for synthesizing a diazaphosphacycle is provided. The method includes reacting a diimine with an acid halide, a diacid dihalide, a sulfonyl halide, a disulfonyl dihalide, a phosphoryl halide, or a diphosphoryl dihalide to form a dihalo intermediate compound. The method further includes reacting the dihalo intermediate compound with a phosphine of formula $R^1$—$PH_2$ in the substantial absence of $O_2$ to form the diazaphosphacycle. In the method, $R^1$ is selected from substituted or unsubstituted aryl groups, substituted or unsubstituted alkyl groups, substituted or unsubstituted alkenyl groups, substituted or unsubstituted cycloalkyl groups, or substituted or unsubstituted ferrocenyl groups; and the diimine has the formula IV

IV where $R^8$ and $R^9$ are independently selected from substituted or unsubstituted aryl groups, substituted or unsubstituted alkyl groups, substituted or unsubstituted cycloalkyl groups, substituted or unsubstituted heterocyclyl groups, or substituted or unsubstituted ferrocenyl groups.

Still other such methods are provided in which the diimine is reacted with a diacyl dihalide, and the diacyl dihalide has the formula V or the formula VI and the diazaphosphacycle has the formula VII or the formula VIII

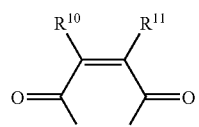

V

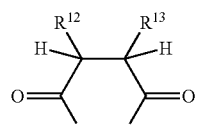

VI

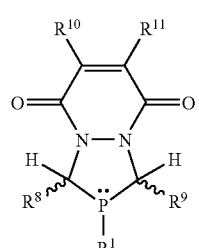

VII

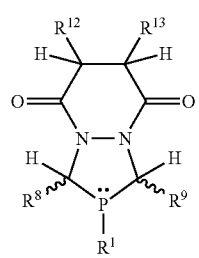

VIII where:

$R^{10}$, $R^{11}$, $R^{12}$, and $R^{13}$ are independently selected from —H, substituted or unsubstituted alkyl groups, substituted or unsubstituted cycloalkyl groups, or substituted or unsubstituted aryl groups;

$R^{10}$ and $R^{11}$ may join together to form a substituted or unsubstituted aryl group or a substituted or unsubstituted cycloalkenyl group;

$R^{12}$ and $R^{13}$ may join together to form a substituted or unsubstituted cycloalkenyl group or a substituted or unsubstituted cycloalkyl group; and X and Z are independently selected from the group consisting of —Cl and —Br.

Other methods are provided in which $R^8$ and $R^9$ are identical but are not part of the same group and in which $R^8$ and $R^9$ are substituted or unsubstituted aryl groups.

Still other methods for synthesizing diazaphosphacycles are provided in which the diacyl dihalide is phthaloyl dichloride.

The invention further provides diazaphosphacycles having the formula III and salts of the diazaphosphacycles.

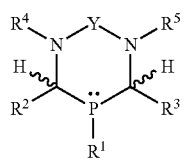

III

In formula III, $R^1$ is selected from substituted or unsubstituted aryl groups, substituted or unsubstituted alkyl groups, substituted or unsubstituted alkenyl groups, substituted or unsubstituted cycloalkyl groups, or substituted or unsubstituted ferrocenyl groups;

$R^2$ and $R^3$ are independently selected from substituted or unsubstituted aryl groups, substituted or unsubstituted alkyl groups, substituted or unsubstituted cycloalkyl groups, substituted or unsubstituted heterocyclyl groups, or substituted or unsubstituted ferrocenyl groups;

$R^4$ is selected from —H, substituted or unsubstituted alkyl groups, substituted or unsubstituted cycloalkyl groups, substituted or unsubstituted aryl groups, trialkylsilyl groups, triarylsilyl groups, alkyldiarylsilyl groups, dialkylarylsilyl groups, —C(═O)—$R^6$ groups, —S(═O)$_2$—$R^6$ groups, —P(═O)$R^6R^7$ groups, or —C(═N$R^6$)—$R^7$ groups;

$R^5$ is selected from —H, substituted or unsubstituted alkyl groups, substituted or unsubstituted cycloalkyl groups, substituted or unsubstituted aryl groups, trialkylsilyl groups, triarylsilyl groups, alkyldiarylsilyl groups, dialkylarylsilyl groups, —C(═O)—$R^7$ groups, —S(═O)$_2$—$R^6$ groups, —P(═O)$R^6R^7$ groups, or —C(═N$R^6$)—$R^7$ groups;

$R^6$ is selected from substituted or unsubstituted alkyl groups, substituted or unsubstituted alkenyl groups, substituted or unsubstituted cycloalkyl groups, substituted or unsubstituted aryl groups, —OH groups, substituted or unsubstituted alkoxy groups, substituted or unsubstituted aryloxy groups, —NH(alkyl) groups, —NH(aryl) groups, —N(aryl)$_2$ groups, —N(alkyl)$_2$ groups, —N(alkyl)(aryl) groups, —S-alkyl groups, or S-aryl groups;

$R^7$ is selected from substituted or unsubstituted alkyl groups, substituted or unsubstituted alkenyl groups, substituted or unsubstituted cycloalkyl groups, substituted or unsubstituted aryl groups, —OH groups, substituted or unsubstituted alkoxy groups, substituted or unsubstituted aryloxy groups, —NH(alkyl) groups, —NH(aryl) groups, —N(aryl)$_2$ groups, —N(alkyl)$_2$ groups, —N(alkyl)(aryl) groups, —S-alkyl groups, or S-aryl groups;

$R^6$ and $R^7$ may be part of the same alkyl group, alkenyl group, or aryl group such that $R^4$ and $R^5$ together with the two nitrogen atoms of the diazaphosphacycle form a ring; and Y is a linking group selected from the group consisting of substituted and unsubstituted cycloalkyl groups, substituted and unsubstituted aryl groups, substituted and unsubstituted alkenyl groups, silyl groups, substituted alkyl groups, and groups having the formula —(CH$_2$)$_n$— where n is selected from 0, 1, 2, or 3.

Still further diazaphosphacycles are provided in which n is 0. Yet other diazaphosphacycles are provided in which $R^4$ and $R^5$ are both —H. Still other diazaphosphacycles are provided in which $R^4$ is a —C(═O)—$R^6$ group and $R^5$ is a —C(═O)—$R^7$ group.

Still further diazaphosphacycles are provided which have the formula IX where $R^1$, $R^2$, and $R^3$ have any of the values set forth above and in which the benzene ring of formula IX may be substituted or unsubstituted

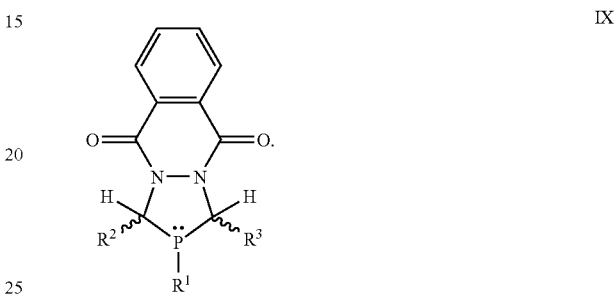

IX

Still further diazaphosphacycles are provided that have the formula IIIA, IIIB, or IIIC as set forth above.

Still further diazaphosphacycles are provided in which the diazaphosphacycle is present as a mixture of enantiomers.

Still further diazaphosphacycles are provided in which Y is a cycloalkyl group. In some diazaphosphacycles where Y is a cycloalkyl group, one of the N atoms is bonded to a first ring member C atom of the cycloalkyl group and the other N atom is bonded to a second ring member C atom that is bonded to the first ring member C atom.

Still other diazaphosphacycles are provided in which Y has the formula

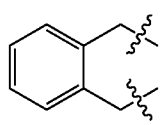

and the benzene ring of Y may be additionally substituted.

The invention further provides diazaphosphacycles having the formula X

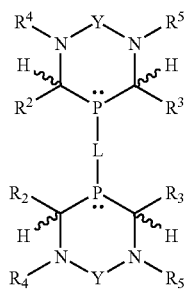

X where L is a linking group selected from substituted or unsubstituted alkyl groups, substituted or unsubstituted alkenyl groups, substituted or unsubstituted aryl groups, or substituted and unsubstituted ferrocenyl groups, and the other variables have the values set forth with respect to the diazaphosphacycles of formula III set forth above. Still other such diazaphosphacycles are provided in which L is selected from ethane, ethylene, propane, benzene, anthracene, 9,10-dihydroanthracene, xanthene, or ferrocene. Transition metal complexes including these diazaphosphacycles are also provided in which at least one of the phosphorus atoms of the diazaphosphacycle is bonded to the transition metal. In other such transition metal complexes two of the phosphorus atoms of the diazaphosphacycle are bonded to the transition metal.

The invention further provides combinatorial libraries that include a collection of different diazaphosphacycles of the present invention.

The invention further provides transition metal complexes that include a diazaphosphacycle according to the invention and a transition metal where the phosphorus atom of the diazaphosphacycle is bonded to the transition metal. Transition metal complexes are further provided in which the transition metal is selected from of Rh, Ru, Pd, Pt, Ir, Ni, Co, or Fe. Still other transition metal complexes are provided in which the transition metal complex has catalytic activity. A method for catalyzing a chemical reaction using a transition metal complex of the present invention as a catalyst is further provided. Furthermore, the invention provides libraries of transition metal complexes that include a collection of different transition metal complexes that include the diazaphosphacycles of the present invention.

Methods for synthesizing diazaphosphacycle transition metal complexes are further provided. The methods include reacting a diazaphosphacycle of the present invention with a starting transition metal complex to produce the diazaphosphacycle transition metal complex. The starting transition metal complex includes at least one ligand that is replaced by the diazaphosphacycle.

Other methods for synthesizing a diazaphosphacycle transition metal complex are provided in which the ligand replaced by the diazaphosphacycle is selected from phosphines; amines; diamines; CO; Cl; Br; nitriles; 1,5-cyclooctadiene, norbornadiene, and other dienes; alkenes; arenes; ketones; alcohols; ethers; thiols; or sulfoxides.

Further objects, features and advantages of the invention will be apparent from the following detailed description when taken in conjunction with the accompanying drawings.

BRIEF DESCRIPTION OF THE DRAWINGS

FIG. 9 is a $^{1}H$ NMR spectrum of a Rh(NBD)(Cl) complex with compound rac-6a.

FIG. 10 is a $^{31}P$ NMR spectrum ($^{1}H$ coupled) of a Rh(NBD)(Cl) complex with compound rac-6a.

FIG. 15 is an X-ray crystal structure ORTEP diagram of a Rh(NBD)(Cl) complex with compound rac-6a.

DETAILED DESCRIPTION OF THE INVENTION

Figure 1:
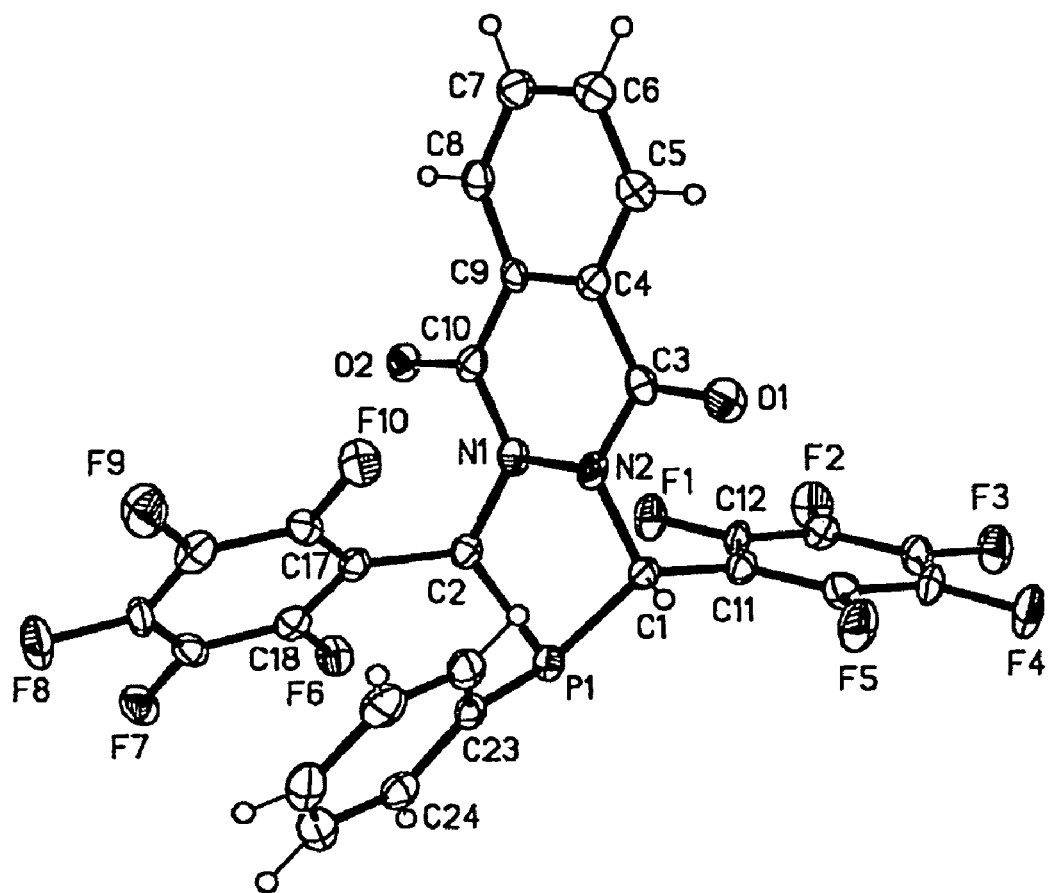
FIG. 1 is an X-ray crystal structure ORTEP diagram of rac-6e with the displacement ellipsoids drawn at the 50% probability level.
Figure 2:
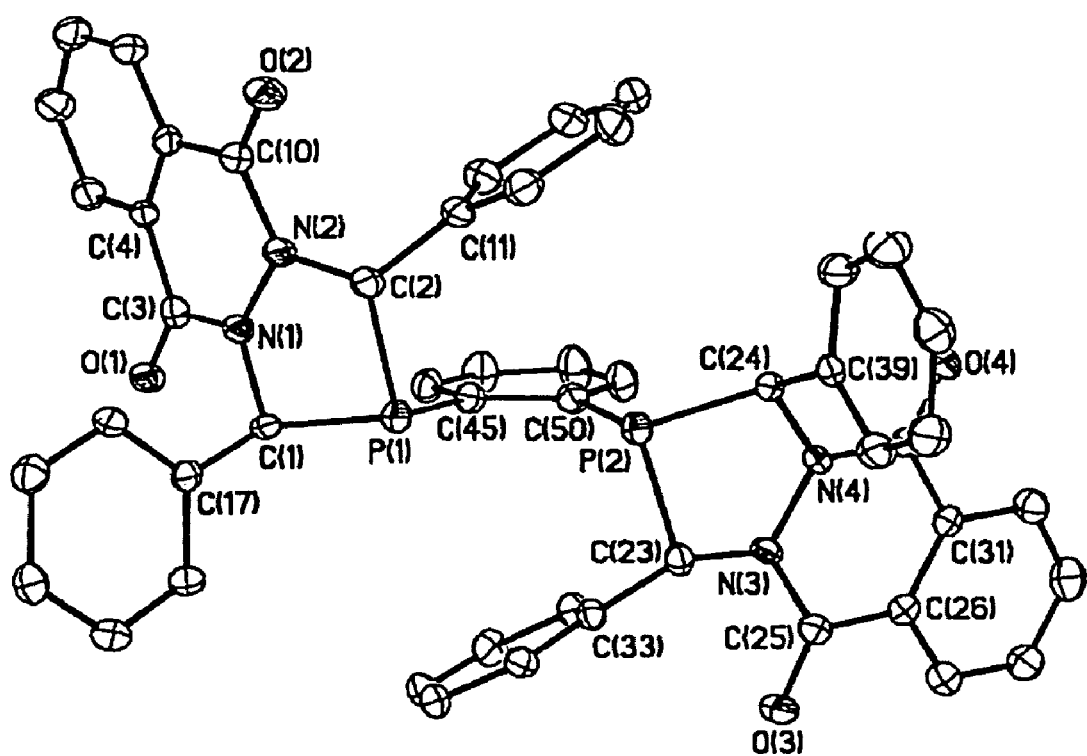
FIG. 2 is an X-ray crystal structure of rac-8. The ORTEP diagram is drawn with 30% probability ellipsoids. Solvent molecules and hydrogens have been removed for clarity.

Generally, the invention provides diazaphosphacycles such as, but not limited to, 3,4-diazaphospholanes, and methods for preparing them. The invention also generally provides transition metal complexes and methods for preparing them from diazaphosphacycles. The metal complexes have catalytic activity and are suitable for use in a wide variety of catalytic transformations such, as, but not limited to, hydrogenation and hydroformylation reactions. The invention also provides libraries of diazaphosphacycles and transition metal complexes including diazaphosphacycles.

Variables used in the chemical formulas are understood to be used consistently throughout. For example, $R^1$ is used to refer to the same groups unless otherwise specifically noted.

The phrase "diazaphosphacycles" refers to a cyclic compound that includes one phosphorus atom and two nitrogen atoms as ring members. The phrase "diazaphospholane" refers to a five membered ring that includes one phosphorus atom and two nitrogen atom ring members. A diazaphospholane is a type of a diazaphosphacycle.

A reaction or method run in the "substantial absence of oxygen" means that the reaction is carried out using standard methodology known to those skilled in the art of working with air-sensitive compounds. This does not require the complete absence of $O_2$ only the absence of enough oxygen so that oxygen does not interfere with the desired reaction. Common procedures for performing a reaction or method in the substantial absence of oxygen include, but are not limited to the use of Schlenk techniques, the use of glove bags or glove boxes, and the use of solvents from which most, if not all, of the oxygen has been removed using standard techniques such as by bubbling an inert gas through the solvent or by freeze-pump-thaw techniques known to those skilled in the art. A reaction performed in the substantial absence of oxygen is generally conducted under an inert atmosphere such as under a $N_2$ or argon atmosphere.

Generally, a reference to a certain element such as hydrogen or H is meant to include all isotopes of that element. For example, a compound having the structure R—PH$_2$ is defined to include those compounds where one or both of the H atoms bonded to the P atom is replaced by a deuterium atom, a tritium atom, or both. An exception to the general definition that reference to a certain element is meant to include all isotopes of that element is when the element is referred to with respect to NMR spectroscopy or a deuterated solvent used in conjunction with NMR spectroscopy.

A wavy line drawn through a line in a structural formula indicates point of attachment of a group.

A wavy line drawn between an atom and a group in a structural formula indicates that a bond exists between the atom and the group, but that the position of the group is not specified. For example a wavy bond between an alkene carbon atom and a group may be used to represent cis and trans isomers, and a wavy bond from an alkyl carbon to a group indicates that no stereochemistry is assigned and the wavy bond may thus be used to represent both S and R configurations at the alkyl carbon.

The acronym "COD" refers to 1,5-cyclooctadiene.

The acronym "NBD" refers to 2,5-norbornadiene also known as bicyclo[2.2.1]hepta-2,5-diene and norbornadiene.

The phrase "unsubstituted alkyl" refers to alkyl groups that do not contain heteroatoms. Thus the phrase includes straight chain alkyl groups such as methyl, ethyl, propyl, butyl, pentyl, hexyl, heptyl, octyl, nonyl, decyl, undecyl, dodecyl and the like. The phrase also includes branched chain isomers of straight chain alkyl groups, including but not limited to, the following which are provided by way of example: —CH($CH_3$)$_2$, —CH($CH_3$)($CH_2CH_3$), —CH($CH_2CH_3$)$_2$, —C($CH_3$)$_3$, —C($CH_2CH_3$)$_3$, —$CH_2$CH($CH_3$)$_2$, —$CH_2$CH($CH_3$)($CH_2CH_3$), —$CH_2$CH($CH_2CH_3$)$_2$, —$CH_2$C($CH_3$)$_3$, —$CH_2$C($CH_2CH_3$)$_3$, —CH($CH_3$)CH($CH_3$)($CH_2CH_3$), —$CH_2CH_2$CH($CH_3$)$_2$, —$CH_2CH_2$CH($CH_3$)($CH_2CH_3$), —$CH_2CH_2$CH($CH_2CH_3$)$_2$, —$CH_2CH_2$C($CH_3$)$_3$, —$CH_2CH_2$C($CH_2CH_3$)$_3$, —CH($CH_3$)$CH_2$CH($CH_3$)$_2$, —CH($CH_3$)CH($CH_3$)CH($CH_3$)$_2$, —CH($CH_2CH_3$)CH($CH_3$)CH($CH_3$)($CH_2CH_3$), and others. Thus, the phrase unsubstituted alkyl groups includes primary alkyl groups, secondary alkyl groups, and tertiary alkyl groups. Preferred unsubstituted alkyl groups include straight and branched chain alkyl groups having 1 to 20 carbon atoms. More preferred such unsubstituted alkyl groups have from 1 to 10 carbon atoms while even more preferred such groups have from 1 to 6 carbon atoms. Most preferred unsubstituted alkyl groups include straight and branched chain alkyl groups having from 1 to 3 carbon atoms and include methyl, ethyl, propyl, and —CH($CH_3$)$_2$.

The phrase "substituted alkyl" refers to an unsubstituted alkyl group as defined above in which one or more bonds to a carbon(s) or hydrogen(s) are replaced by a bond to non-hydrogen and non-carbon atoms such as, but not limited to, a halogen atom in halides such as F, Cl, Br, and I; an oxygen atom in groups such as hydroxyl groups, alkoxy groups, aryloxy groups, and ester groups; a sulfur atom in groups such as thiol groups, alkyl and aryl sulfide groups, sulfone groups, sulfonyl groups, and sulfoxide groups; a nitrogen atom in groups such as amines, amides, alkylamines, dialkylamines, arylamines, alkylarylamines, diarylamines, N-oxides, imides, and enamines; a silicon atom in groups such as trialkylsilyl groups, dialkylarylsilyl groups, alkyldiarylsilyl groups, and triarylsilyl groups; a phosphorus atom in groups such as phosphines, and phosphoryls; and other heteroatoms in various other groups. Substituted alkyl groups also include groups in which one or more bonds to a carbon(s) or hydrogen(s) atom is replaced by a bond to a heteroatom such as oxygen in carbonyl, carboxyl, and ester groups; nitrogen in groups such as imines, oximes, hydrazones, and nitriles. Substituted alkyl groups include, among others, alkyl groups in which one or more bonds to a carbon or hydrogen atom is/are replaced by one or more bonds to fluorine atoms. Other alkyl groups include those in which one or more bonds to a carbon or hydrogen atom is replaced by a bond to an oxygen atom such that the substituted alkyl group contains a hydroxyl, alkoxy, aryloxy, or heterocyclyloxy group. Still other substituted alkyl groups include alkyl groups that have an amine group.

The phrase "unsubstituted alkenyl" refers to an "unsubstituted alkyl" group as defined above where at least one single C—C bond of the unsubstituted alkyl group is replaced by a double bond.

The phrase "substituted alkenyl" has the same meaning with respect to unsubstituted aryl groups that substituted alkyl groups has with respect to unsubstituted alkyl groups.

The phrase "unsubstituted cycloalkyl" refers to a cycloalkyl group where none of the carbon atoms of the cycloalkyl ring is bonded to an element other than H except for the carbon atom(s) bonded as the point of attachment. Examples of unsubstituted cycloalkyl groups include cyclopropyl, cyclobutyl, cyclopentyl, cyclohexyl, cycloheptyl, and cyclooctyl groups. Cyclohexyl and cyclopentyl groups are preferred cycloalkyl groups.

The phrase "substituted cycloalkyl" has the same meaning with respect to unsubstituted cycloalkyl groups that substituted alkyl groups have with respect to unsubstituted alkyl groups. However, a substituted cycloalkyl group also includes cycloalkyl groups in which one or more ring carbon atoms of the cycloalkyl group is bonded to a substituted and/or unsubstituted alkyl group. Thus, the phrase "substituted cycloalkyl" includes, but is not limited to methylcyclohexyl, and chlorocyclopentyl groups among others.

The phrase "unsubstituted aryl" refers to aryl groups that are not substituted. Thus the phrase includes, but is not limited to, groups such as phenyl, biphenyl, anthracenyl, naphthenyl, and xanthenyl by way of example. Although the phrase "unsubstituted aryl" includes groups containing condensed rings such as naphthalene, it does not include aryl groups that have other groups such as alkyl or halo groups bonded to one of the ring members as aryl groups such as tolyl are substituted aryl groups. A preferred unsubstituted aryl group is phenyl. Unsubstituted aryl groups may be bonded to one or more atom in the parent structural formula.

The phrase "substituted aryl group" has the same meaning with respect to unsubstituted aryl groups that substituted alkyl groups have with respect to unsubstituted alkyl groups. However, a substituted aryl group also includes aryl groups in which one or more aromatic carbons of the aryl group is bonded to a substituted and/or unsubstituted alkyl group. Thus, the phrase "substituted aryl" includes, but is not limited to tolyl, and hydroxyphenyl among others.

All ranges recited herein include all combinations and subcombinations included within that range's limits. For example, a temperature range of from about 20° C. to about 65° C. includes ranges of from 20° C. to 60° C., of from 25° C. to 30° C., of from 25° C. to 28° C., and of from 20° C. to 30° C., etc. Furthermore, one skilled in the art will recognize that any listed range can be easily recognized as sufficiently describing and enabling the same range being broken down into at least equal halves, thirds, quarters, fifths, tenths, etc. As a non-limiting example, each range discussed herein can be readily broken down into a lower third, middle third, and upper third.

An acid chloride refers to a compound having at least one carboxylic acid group where the —OH group of the carboxylic acid moiety is replaced with a halogen group such as, but not limited to, —Cl or -Br. A diacid dichloride is a type of acid chloride and refers to a compound having at least two carboxylic acid groups where the —OH groups have been replaced with halogen groups. Examples of diacid dichlorides include, but are not limited to, oxalyl chloride, phthaloyl dichloride, and phthaloyl dibromide.

A method of synthesizing a diazaphosphacycle includes reacting a phosphine with a diimine and optionally one or more equivalents of an acid halide, a sulfonyl halide, a phosphoryl halide, or an acid anhydride in the substantial absence of $O_2$ to form the diazaphosphacycle. The phosphine has the formula I

   I $R^1$ is selected from substituted or unsubstituted aryl groups, substituted or unsubstituted alkyl groups, substituted or unsubstituted alkenyl groups, substituted or unsubstituted cycloalkyl groups, or substituted or unsubstituted ferrocenyl groups. Preferred $R^1$ groups include substituted and unsubstituted phenyl groups and substituted and unsubstituted cycloalkyl groups such as, but not limited to substituted and unsubstituted cyclopentyl groups and cyclohexyl groups. Other preferred $R^1$ groups include one or more —$PH_2$ group such that the phosphine is a polyphosphine. Employing a polyphosphine in the method provides for the production of bidentate ligands. Examples of suitable polyphosphines for use in the methods of the invention include, but are not limited to, 1,2-diphosphinoethane, 1,2-diphosphinoethylene, 1,3-diphosphinopropane, substituted or unsubstituted 1,2-diphosphinobenzene groups, substituted or unsubstituted 1,8-diphosphinoanthracene groups, substituted or unsubstituted 1,8-diphosphino-9,10-dihydroanthracene groups, substituted or unsubstituted 1,8-diphosphinoxanthene groups, or 1,1'-diphosphinoferrocene groups.

The reaction of a diimine with a phosphine of formula I is preferably conducted in a solvent such as, but not limited to, a substantially deoxygenated ether such as diethyl ether or tetrahydrofuran; a substantially deoxygenated alcohol such as ethanol or methanol; substantially deoxygenated water; or substantially deoxygenated dichloroethane. An acid is preferably present when the diimine reacts with the phosphine of formula I. Examples of suitable acids include, but are not limited to hydrochloric acid and hydrobromic acid.

Although not required, in certain preferred methods according the invention, the diimine and the phosphine are reacted in the presence of the optional acid halide, the sulfonyl halide, the phosphoryl halide, or the acid anhydride. The presence of one of the optional halides or anhydride provides for carboxylation, phosphorylation, or sulfonylation of one or both of the N atoms in diazaphosphacycle ring. In some preferred embodiments, the method is conducted in the presence of an acid halide such as, but not limited to acetyl chloride, acetyl bromide, phthaloyl dichloride, or phthaloyl dibromide. In other preferred embodiments, the reaction is conducted in the presence of a diacid dihalide such as phthaloyl dichloride or phthaloyl dibromide. In still other preferred embodiments, the reaction of the diimine with the phosphine is conducted in the presence of an acid anhydride.

The reaction between the diimine and the phosphine is typically conducted at temperatures ranging from less than 0° C. to about 50° C. More preferably, the reaction is conducted at temperatures ranging from at or about 0° C. to at or about 25° C.

In preferred methods of synthesizing diazaphosphacycles, the diimine reacted with the phosphine of formula I has the formula II. In such methods, the diazaphosphacycle formed has the formula III

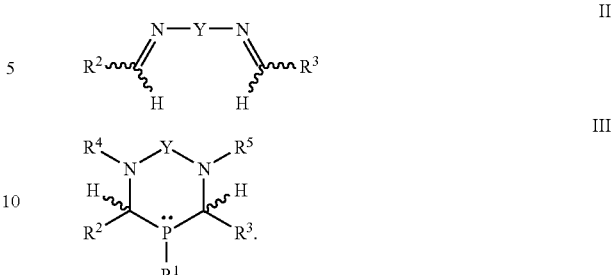

$R^2$ and $R^3$ are independently selected from substituted or unsubstituted aryl groups, substituted or unsubstituted alkyl groups, substituted or unsubstituted cycloalkyl groups, substituted or unsubstituted heterocyclyl groups, or substituted or unsubstituted ferrocenyl groups. In some preferred methods and diazaphosphacycles of the invention, $R^2$ and $R^3$ are identical, but are not part of the same group. In other words, if $R^2$ is a phenyl group, then $R^3$ is another phenyl group. Preferred $R^2$ and $R^3$ groups include phenyl, 2-furanyl, protected pyrrolyl, n-propyl, i-propyl, t-butyl, ferrocenyl, o-hydroxyphenyl, o-tolyl, 2-naphthyl, and pentafluorophenyl groups.

$R^4$ is selected from —H, substituted or unsubstituted alkyl groups, substituted or unsubstituted cycloalkyl groups, substituted or unsubstituted aryl groups, trialkylsilyl groups, triarylsilyl groups, alkyldiarylsilyl groups, dialkylarylsilyl groups, —C(=O)—$R^6$ groups, —S(=O)$_2$—$R^6$ groups, —P(=O)$R^6R^7$ groups, or —C(=N$R^6$)—$R^7$ groups. Preferred $R^4$ groups include —H, and —C(=O)—$R^6$ groups.

$R^5$ is selected from —H, substituted or unsubstituted alkyl groups, substituted or unsubstituted cycloalkyl groups, substituted or unsubstituted aryl groups, trialkylsilyl groups, triarylsilyl groups, alkyldiarylsilyl groups, dialkylarylsilyl groups, —C(=O)—$R^7$ groups, —S(=O)$_2$—$R^7$ groups, —P(=O)$R^6R^7$ groups, or —C(=N$R^6$)—$R^7$ groups. Preferred $R^5$ groups include —H and —C(=O)—$R^7$ groups. In some preferred methods and diazaphosphacycles, $R^4$ is a —C(=O)—$R^6$ group and $R^5$ is a —C(=O)—$R^7$ group.

$R^6$ is selected from substituted or unsubstituted alkyl groups, substituted or unsubstituted alkenyl groups, substituted or unsubstituted cycloalkyl groups, substituted or unsubstituted aryl groups, —OH groups, substituted or unsubstituted alkoxy groups, substituted or unsubstituted aryloxy groups, —NH(alkyl) groups, —NH(aryl) groups, —N(aryl)$_2$ groups, —N(alkyl)$_2$ groups, —N(alkyl)(aryl) groups, —S-alkyl groups, or S-aryl groups.

Preferred $R^6$ groups include alkyl groups such as methyl, ethyl, propyl, butyl, pentyl, and hexyl groups and groups where $R^6$ and $R^7$ join together with the two ring nitrogen atoms of the diazaphosphacycle to form a ring.

$R^7$ is selected from substituted or unsubstituted alkyl groups, substituted or unsubstituted alkenyl groups, substituted or unsubstituted cycloalkyl groups, substituted or unsubstituted aryl groups, —OH groups, substituted or unsubstituted alkoxy groups, substituted or unsubstituted aryloxy groups, —NH(alkyl) groups, —NH(aryl) groups, —N(aryl)$_2$ groups, —N(alkyl)$_2$ groups, —N(alkyl)(aryl) groups, —S-alkyl groups, or S-aryl groups.

Preferred $R^7$ groups include alkyl groups such as methyl, ethyl, propyl, butyl, pentyl, and hexyl groups and groups where, as indicated above, $R^6$ and $R^7$ join together with the two ring nitrogen atoms of the diazaphosphacycle to form a ring $R^6$ and $R^7$ may be part of the same alkyl group, alkenyl group, or aryl group such that $R^4$ and $R^5$ together with the two nitrogen atoms of the diazaphosphacycle form a ring. Preferred such compounds include those where the ring formed has 6 ring members.

Y is a linking group selected from substituted or unsubstituted cycloalkyl groups, substituted or unsubstituted aryl groups, substituted or unsubstituted alkenyl groups, silyl groups, substituted alkyl groups, or groups having the formula $-(CH_2)_n-$ wherein n is selected from the group consisting of 0, 1, 2, and 3. In some preferred methods and diazaphosphacycles, Y is a $-(CH_2)_n-$ group where n is 0. In such compounds the nitrogen atoms of the diazaphosphacycle are directly bonded to one another and the compound is a 3,4-diazaphospholane. In other preferred methods and diazaphosphacycles, Y is a cycloalkyl group and one of the nitrogen atoms of the diimine is bonded to a first ring member carbon atom of the cycloalkyl group and the other nitrogen atom of the diimine is bonded to a second ring member carbon atom. Furthermore, in such preferred compounds, the second ring member carbon atom of the cycloalkyl group is directly bonded to the first ring member carbon atom of the cycloalkyl group such that the cycloalkyl group is a 1,2-disubstituted cycloalkyl group such as a 1,2-disubstituted cyclohexyl group. Both cis and trans 1,2-disubstituted alkyl groups are preferred. Other preferred Y groups have the following formula where the benzene ring of the group may be further substituted:

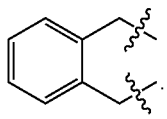

In other preferred methods and diazaphosphacycles, the diazaphosphacycle has the formula IIIA, the formula IIIB, or is a mixture of diazaphosphacycles of formulas IIIA and IIIB. Such diazaphosphacycles are generally referred to as rac compounds. In more preferred such diazaphosphacycles, Y is a $-(CH_2)_n-$ group where n is 0.

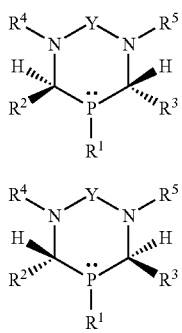

In other preferred methods and diazaphosphacycles, the diazaphosphacycle has the formula IIIC. Such compounds are generally referred to as meso compounds. In more preferred such compounds, Y is a $-(CH_2)_n-$ group where n is 0 so that the ring nitrogen atoms of the diazaphosphacycle are directly bonded to one another.

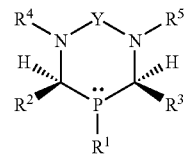

The methods disclosed herein may be used to produce diazaphosphacycles where both $R^4$ and $R^5$ are —H. Such a method typically involves reaction of the phosphine of formula I with the diimine of formula II in the absence of acid halide, acid anhydride, sulfonyl halide, and/or phosphoryl halide. When such a method is used, the method may include the later addition of an acid halide, an acid anhydride, a sulfonyl halide, or a phosphoryl halide. Preferably an acid halide or an acid anhydride is used in such a method. The later addition of one of the above-specified reagents forms a second diazaphosphacycle in which at least one of $R^4$ and $R^5$ is not —H. In other preferred such methods, neither $R^4$ nor $R^5$ is an —H in the second diazaphosphacycle.

The widely different groups that may be used for $R^1$-$R^6$ and Y in the method of the invention allows a library of different diazaphosphacycles to be produced from readily available starting materials. Such a library may be produced using standard combinatorial methods allowing for the production of large numbers of diazaphosphacycles.

A first alternative method of synthesizing a diazaphosphacycle includes reacting a diimine with an acid halide, a diacid dihalide, a sulfonyl halide, a disulfonyl dihalide, a phosphoryl halide, or a diphosphoryl dihalide to form a dihalo intermediate compound. The method further includes reacting the dihalo intermediate compound with a phosphine of formula $R^1$—$PH_2$ in the substantial absence of $O_2$ to form the diazaphosphacycle. In the method, $R^1$ is selected from substituted or unsubstituted aryl groups, substituted or unsubstituted alkyl groups, substituted or unsubstituted alkenyl groups, substituted or unsubstituted cycloalkyl groups, or substituted or unsubstituted ferrocenyl groups; and the diimine has the formula IV

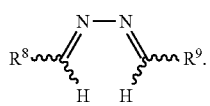

$R^8$ and $R^9$ are independently selected from substituted or unsubstituted aryl groups, substituted or unsubstituted alkyl groups, substituted or unsubstituted cycloalkyl groups, substituted or unsubstituted heterocyclyl groups, or substituted or unsubstituted ferrocenyl groups. Any of the reaction conditions suitable for the previously described method may be used in conjunction with this first alternative method. In some preferred such methods and diazaphosphacycles produced therefrom, $R^8$ and $R^9$ are identical, but are not part of the same group. In other words, if $R^8$ is a phenyl group, then $R^9$ is another phenyl group. Preferred $R^8$ and $R^9$ groups include phenyl, 2-furanyl, protected pyrrolyl, n-propyl, i-propyl, t-butyl, ferrocenyl, o-hydroxyphenyl, o-tolyl, 2-naphthyl, and pentafluorophenyl groups. Substituted and unsubstituted aryl groups are particularly suitable as $R^8$ and $R^9$ groups.

Still other such methods are provided in which the diimine is reacted with a diacyl dihalide, and the diacyl dihalide has the formula V or the formula VI and the diazaphosphacycle has the formula VII or the formula VIII V
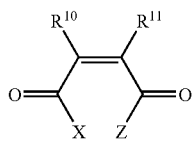

VI
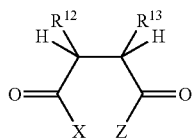

VII
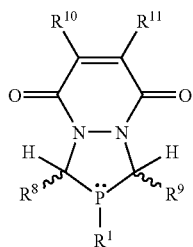

VIII
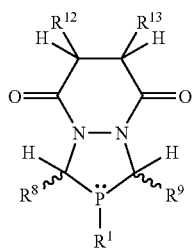

$R^{10}$, $R^{11}$, $R^{12}$, and $R^{13}$ are independently selected from —H, substituted or unsubstituted alkyl groups, substituted or unsubstituted cycloalkyl groups, or substituted or unsubstituted aryl groups. $R^{10}$ and $R^{11}$ may further join together to form a substituted or unsubstituted aryl group or a substituted or unsubstituted cycloalkenyl group. Similarly, $R^{12}$ and $R^{13}$ may join together to form a substituted or unsubstituted cycloalkenyl group or a substituted or unsubstituted cycloalkyl group.

X and Z are independently selected from —Cl or —Br.

In particularly preferred methods for synthesizing diazaphosphacycles according to the alternative method, phthaloyl dichloride is the diacyl dihalide of formula V.

Preferred diazaphosphacycles include any of the compounds having the formulas II, IIIA, IIIB, IIIC, VII, or VIII produced by any of the methods of the present invention. Preferred diazaphosphacycles of the invention further include compounds of the formula IX IX
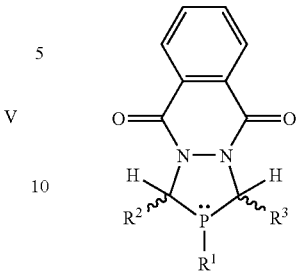

where $R^1$, $R^2$, and $R^3$ have any of the values set forth above with respect to formula III.

Preferred diazaphosphacycles of formula III include those having the formula X

X
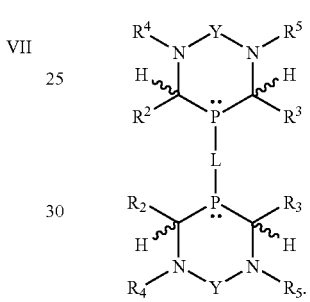

In compounds of formula X, L is a linking group selected from substituted or unsubstituted alkyl groups, substituted or unsubstituted alkenyl groups, substituted or unsubstituted aryl groups or substituted or unsubstituted ferrocenyl groups. Preferred L groups include ethane, ethylene, propane, benzene, anthracene, 9,1-dihydroanthracene, xanthene, and ferrocene. In more preferred such diazaphosphacycles, Y is a —$(CH_2)_n$— group where n is 0.

Scheme 1 shows how various 3,4-diazaphosphacycles may be synthesized from simple starting materials to provide a large number of chiral phosphine ligands.

Scheme 1

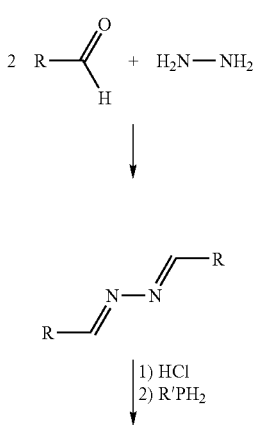

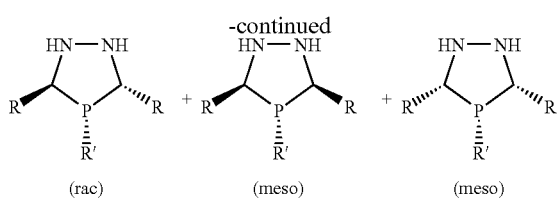

R = Ph, o-tolyl, 2-furanyl,
  2-Naphthyl,
  2-(EtOCH$_2$O)-phenyl,
  n-Pr, i-Pr, $^t$Bu
R' = Ph, cyclohexyl As shown in Scheme 1, the reaction of 2 equivalents of an aldehyde such as aldehydes where R is an alkyl group or aryl group with a diamine such as hydrazine readily affords the diimines for use in the method for producing the diazaphosphacycles. An excess of aldehyde may be used to produce the diimine. The reaction shown in Scheme 1 may be carried out in a rac selective manner. The reaction typically provides high yields in excess of 80 percent of the 3,4-diazaphospholanes.

Scheme 2 shows the synthesis of numerous different diazaphosphacycles from simple and readily available diimines and phosphines. The diimine is formed from hydrazine and the appropriate aldehyde. Thus, the diimine is a compound of formula II as described above, where Y is a —(CH$_2$)$_n$— group where n is 0.

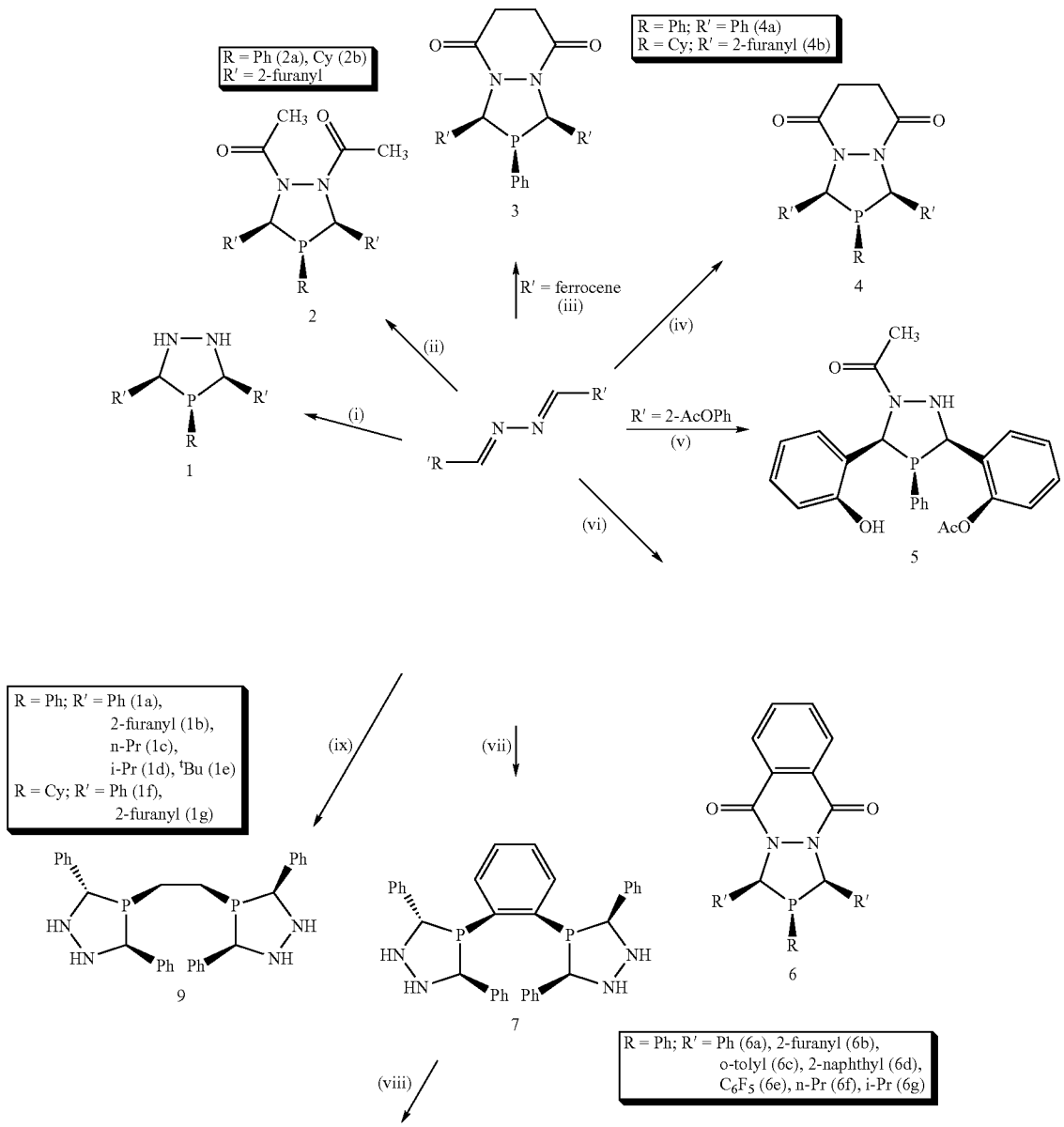

-continued

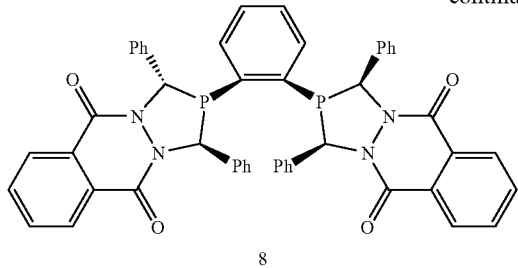

8 a(i) HCl, RPH$_2$, (ii) CH$_3$COCl, RPH$_2$ (iii) succinyl chloride, PhPH$_2$ (iv) succinyl chloride, RPH$_2$ (v) HCl, PhPH$_2$ (vi) phthaloyl chloride, PhPH$_2$ (vii) HCl, 1,2-(PH$_2$)$_2$C$_6$H$_4$ (viii) phthaloyl chloride in THF (ix) HCl, PH$_2$CH$_2$CH$_2$PH$_2$. All the reaction products were worked up with 10% K$_2$CO$_3$.

The condensation of azines (R$^2$—CH═N—N═CH—R$^3$), shown generically as formula II, prepared by the reaction of hydrazine with 2 equivalents of the corresponding aldehyde, as shown in Scheme 1, and primary phosphines yields diazaphosphacycles such as compound 1. As set forth in Scheme 2, this procedure surprisingly and unexpectedly provides a variety of 3,4-diazaphospholanes in good yields (25-95%) and rac selectivity under mild reaction conditions.

Condensation of an azine and a primary phosphine preferably with 1 equivalent of dry HCl as an acid promoter affords simple 3,4-diazaphospholanes (1, 7, 9). In preferred embodiments, acid chlorides are employed and function as both promoters and N-functionalization reagents to provide N,N'-dicarboxyl-3,4-diazaphospholanes (2, 3, 4, 6) directly in a one-step synthesis as illustrated in Scheme 2. Reaction of the azine derived from acetyl salicylaldehyde with phenylphosphine yielded 5, a product in which one of the salicyl acetyl groups was transferred to the hydrazine moiety. As exemplified by the transformation of compound 7 to compound 8, 3,4-diazaphospholanes and acid chlorides react cleanly to provide a wide variety of N,N'-dicarboxyl-3,4-diazaphospholanes. The N,N'-dicarboxyl-3,4-diazaphospholanes exhibit higher thermal and chemical stability than simple 3,4-diazaphospholanes, although both are suitable for forming transition metal complexes.

Acid-promoted addition of primary phosphines to diimines are generally rac selective, but the reaction is sensitive to the selection of the R$^1$ group of the phosphine and to the selection of the R$^2$, R$^3$, R$^8$, and R$^9$ groups of the diimine used. For example, where R$^1$ is phenyl, rac/meso ratios (0.6-30:1) are dependent on the choice of R$^2$ and R$^3$ or R$^8$ and R$^9$. However, when R$^1$ is a cyclohexyl group, then formation of the rac isomers are highly preferred and in some cases are the only isomers observed. Azines derived from bulky, electron withdrawing substituents such as pentafluorophenyl and ferrocenyl generally yield low rac/meso ratios (6e, 2:1; 3, 0.6:1). For most diazaphospholanes, simple recrystallization provides separation of diastereomers (e.g., rac/meso ratios 30:1 for 1a). The diazaphosphacycles were characterized by X-ray crystallography and $^1$H and $^{31}$P NMR spectroscopy as shown in FIGS. 1, 2, and 4-6.

Resolution of enantiomeric mixtures may be accomplished by various methods known to those skilled in the art. Resolution of racemic diazaphospholanes 1a, 1e, and 9 was accomplished by N-functionalization with di-O-methyl-L-tartaric acid dichloride to form bicyclic diastereomers followed by chromatographic separation on silica gel.

Scheme 3 shows how various functionalized 3,4-diazaphospholanes may be prepared from a diimine such as a diimine of formula II where Y is a —(CH$_2$)$_n$— group and n is 0.

Scheme 3

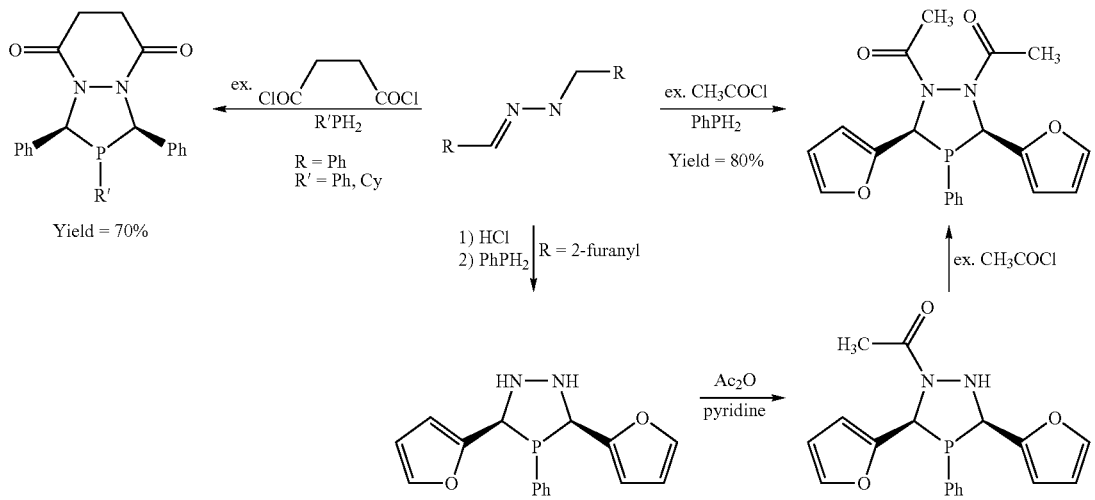

Scheme 4 shows a synthetic route for obtaining rigid bicyclic 3,4-diazaphospholanes from a diimine of formula II where Y is a —(CH$_2$)$_n$— group and n is 0.

Scheme 4

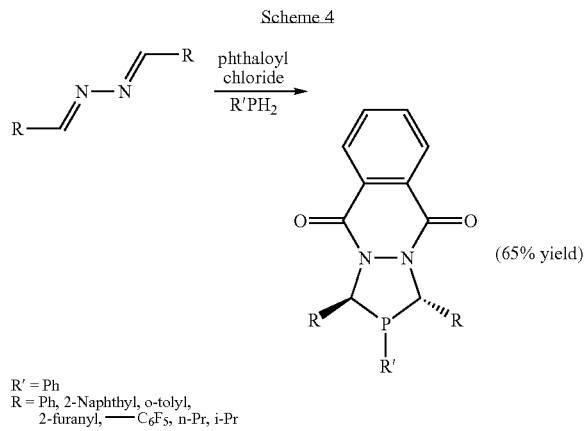

R' = Ph
R = Ph, 2-Naphthyl, o-tolyl, 2-furanyl, —C$_6$F$_5$, n-Pr, i-Pr

Scheme 5 shows a synthetic method that may be used for preparing a diazaphosphacycle that includes a hydroxyphenyl group.

Scheme 5

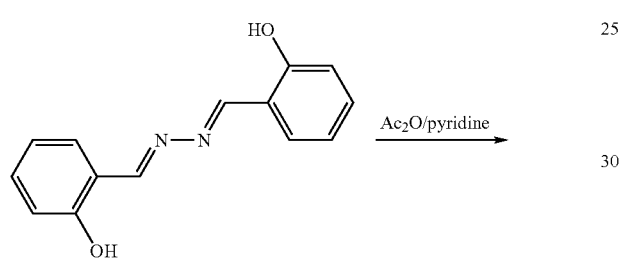

-continued

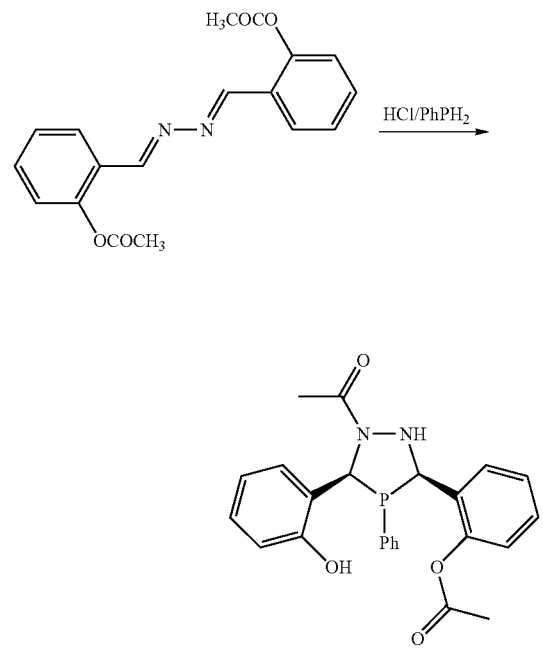

Scheme 6 shows a synthetic method for preparing a sterically demanding diazaphosphacycle that includes two ferrocenyl groups. As can be seen in Scheme 6, one of the products is thermally unstable and can be degraded.

Scheme 6

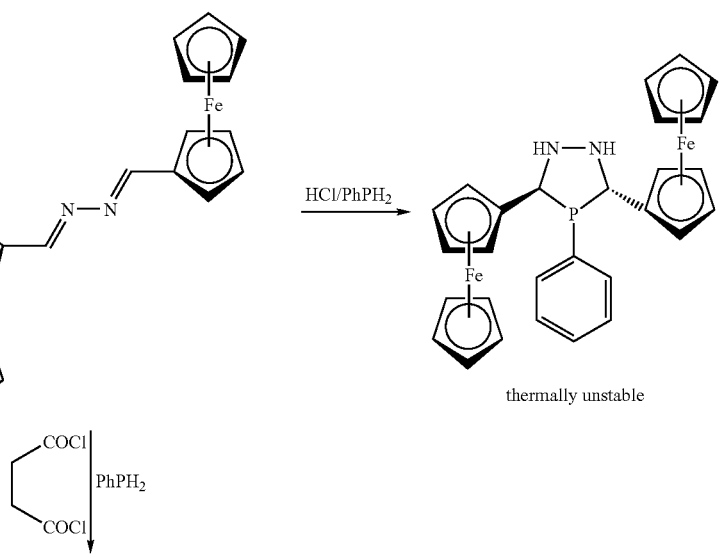

thermally unstable

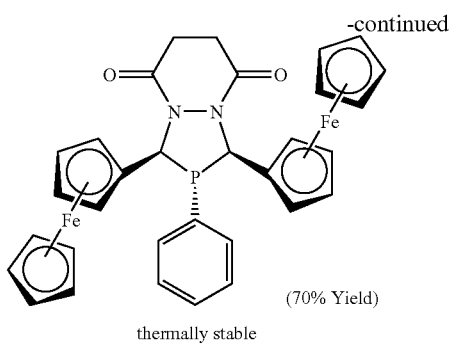

(70% Yield)

thermally stable

Figure 3:
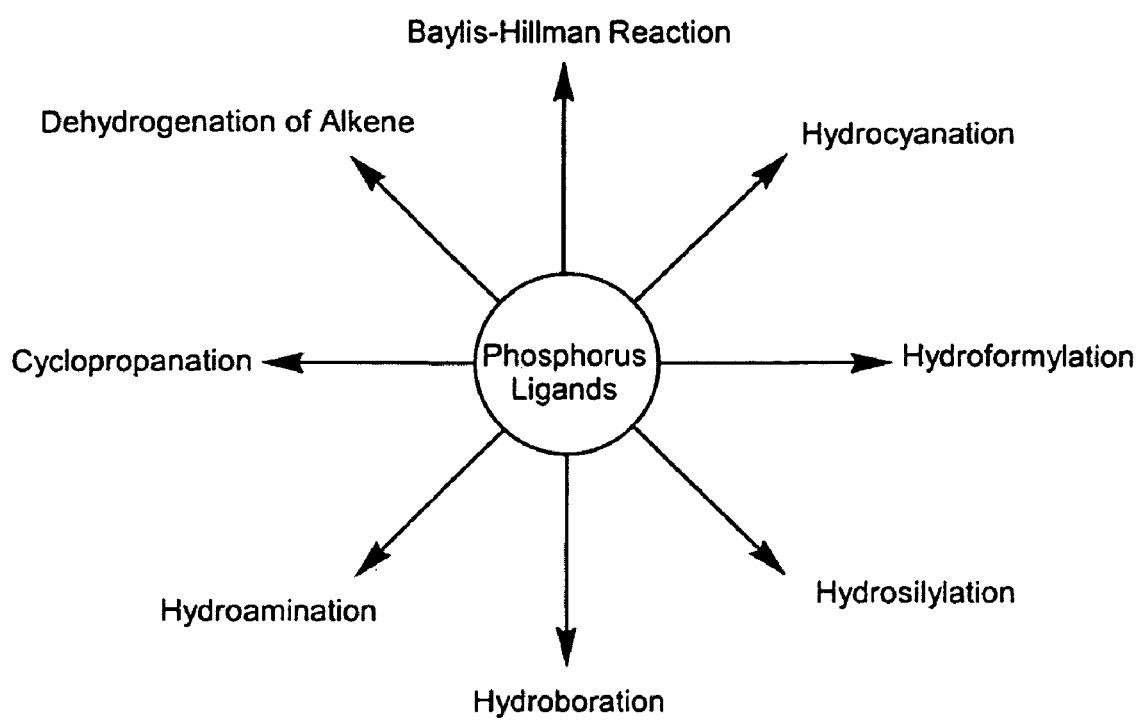
FIG. 3 is a diagram showing a few of the catalytic reactions that metal complexes with phosphorus ligands catalyze.
Figure 4:
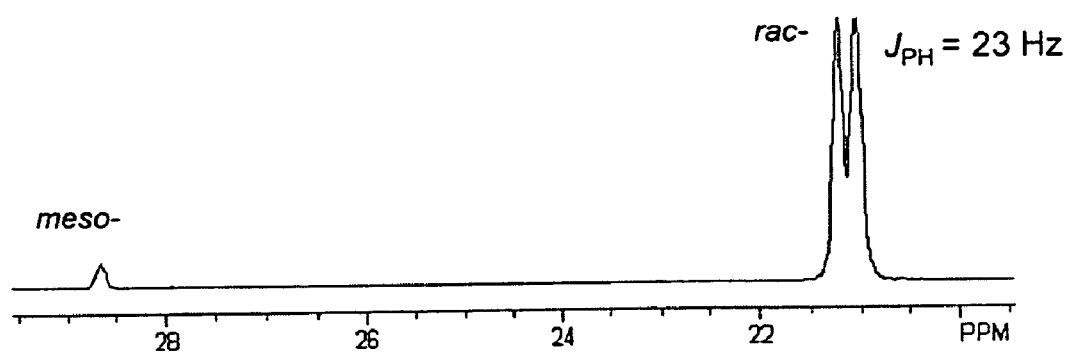
FIG. 4 is a $^{31}P$ NMR spectrum ($^{1}H$ coupled) of compound 1a with a rac:meso ratio of about 30:1.
Figure 5:
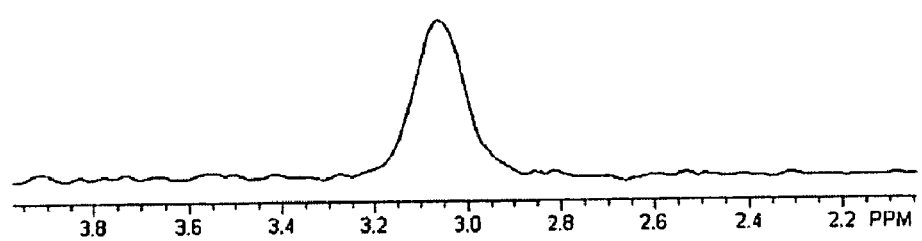
FIG. 5 is a $^{31}P$ NMR spectrum ($^{1}H$ coupled) of meso-3.
Figure 6:
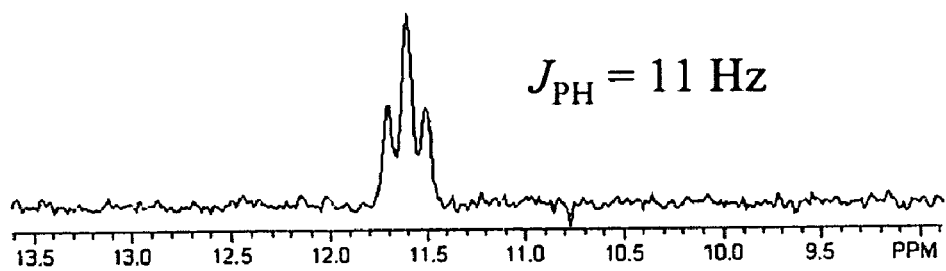
FIG. 6 is a $^{31}P$ NMR spectrum ($^{1}H$ coupled) of compound 7.
Figure 7:
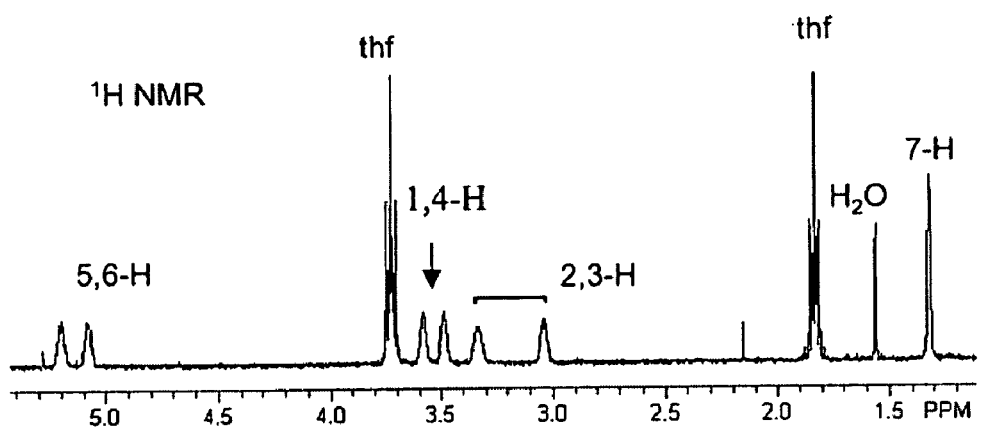
FIG. 7 is a $^{1}H$ NMR spectrum of a Rh(NBD)(Cl) complex with compound rac-6b.

The diazaphosphacycles of the present invention may be combined with a transition metal to form a transition metal complex. The transition metal complexes of the invention include a transition metal and a diazaphosphacycle where at least one phosphorus atom in the diazaphosphacycle is bonded to the transition metal. Preferred metal complexes are prepared using 3,4-diazaphospholanes. In preferred transition metal complexes including a diazaphosphacycle of formula X, two of the phosphorus atoms are bonded to the transition metal. Preferred transition metals in transition metal complexes include Rh, Ru, Pd, Pt, Ir, Ni, Co, and Fe. Other preferred transition metal complexes have catalytic activity and can be used to catalyze transformations such as those carried out with known transition metal complexes as understood by those skilled in the art. Just a few of the catalytic transformations possible with the transition metal complexes of the present invention are shown in FIG. 3.

Because the methods of the present invention may be used to readily synthesize a plethora of diazaphosphacycles, libraries of these compounds and transition metal complexes prepared from them may be formed.

Various methods may be used to prepare transition metal complexes from the diazaphosphacycles of the present invention. Such methods include reacting a diazaphosphacycle with a starting transition metal complex to produce the diazaphosphacycle transition metal complex. In such reactions, the starting transition metal complex typically includes at least one ligand that is replaced by the diazaphosphacycle during the reaction. Examples of ligands include phosphines; amines; diamines; CO; Cl, Br; nitriles such as, but not limited to acetonitrile and benzonitrile; 1,5-cyclooctadiene, norbornadiene, and other dienes; alkenes; ketones; alcohols; ethers; thiols; and sulfoxides.

Figure 14:
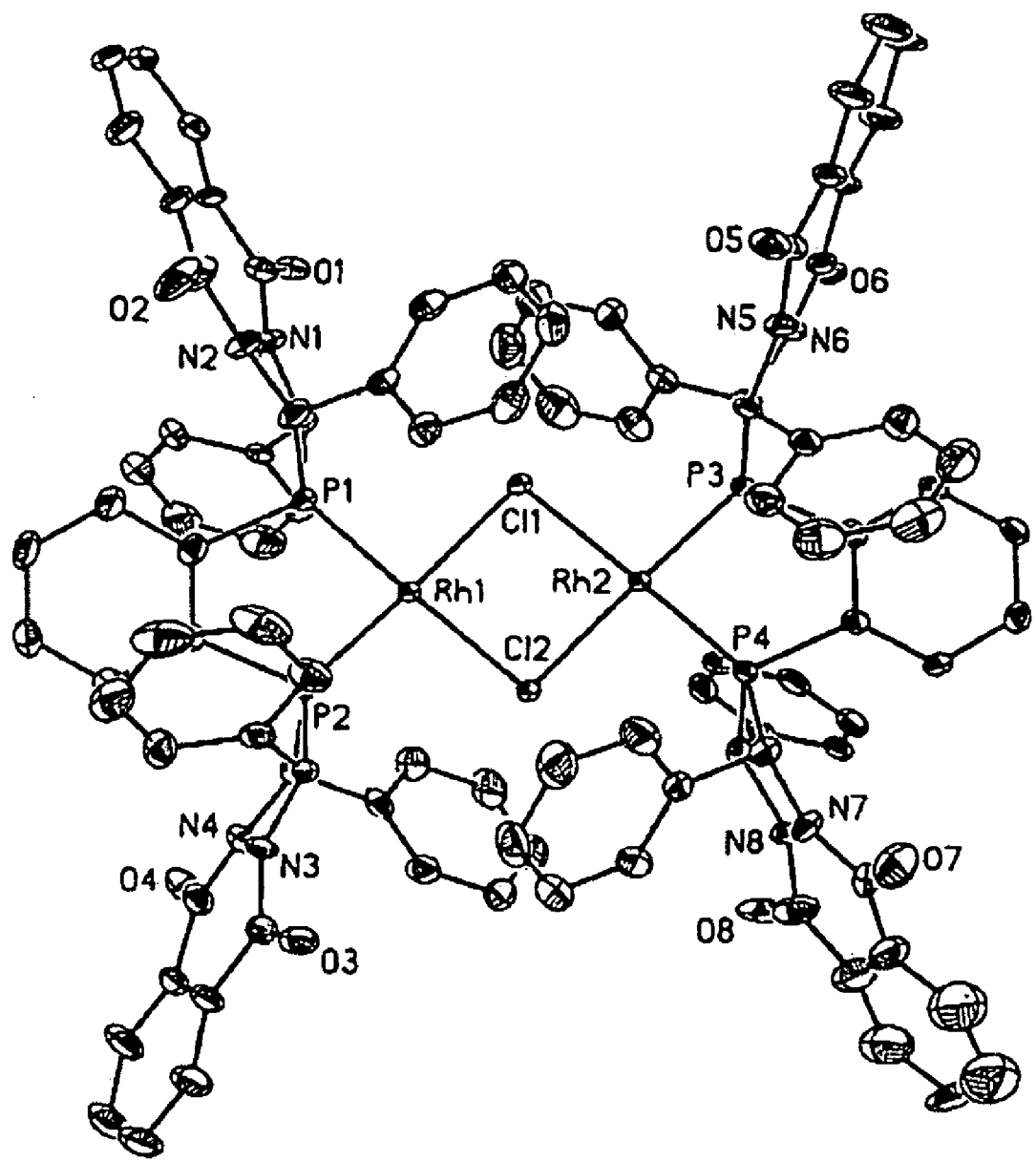
FIG. 14 is an X-ray crystal structure ORTEP diagram of [{1,2-bis(diazaphospholanes)benzene}RhCl]$_2$ where the 1,2-bis(diazaphospholane)benzene is compound 8.
Figure 15:
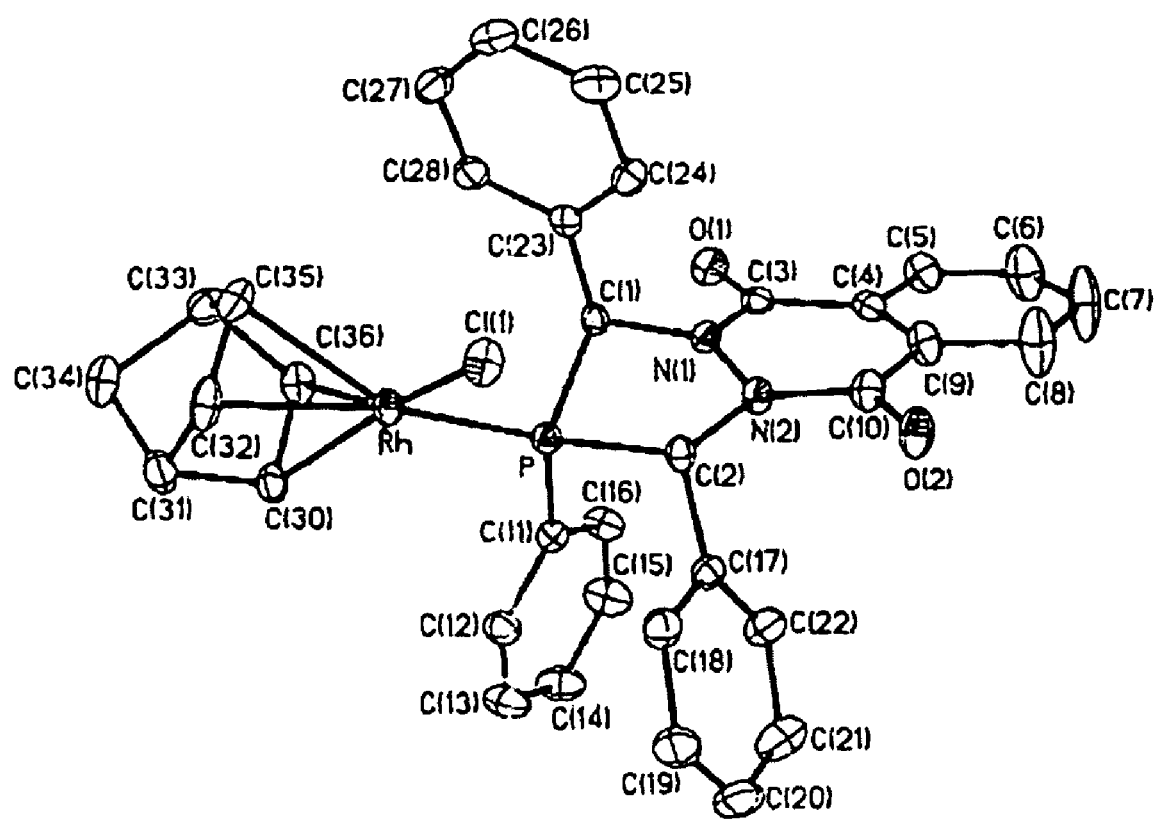
Figure 16:
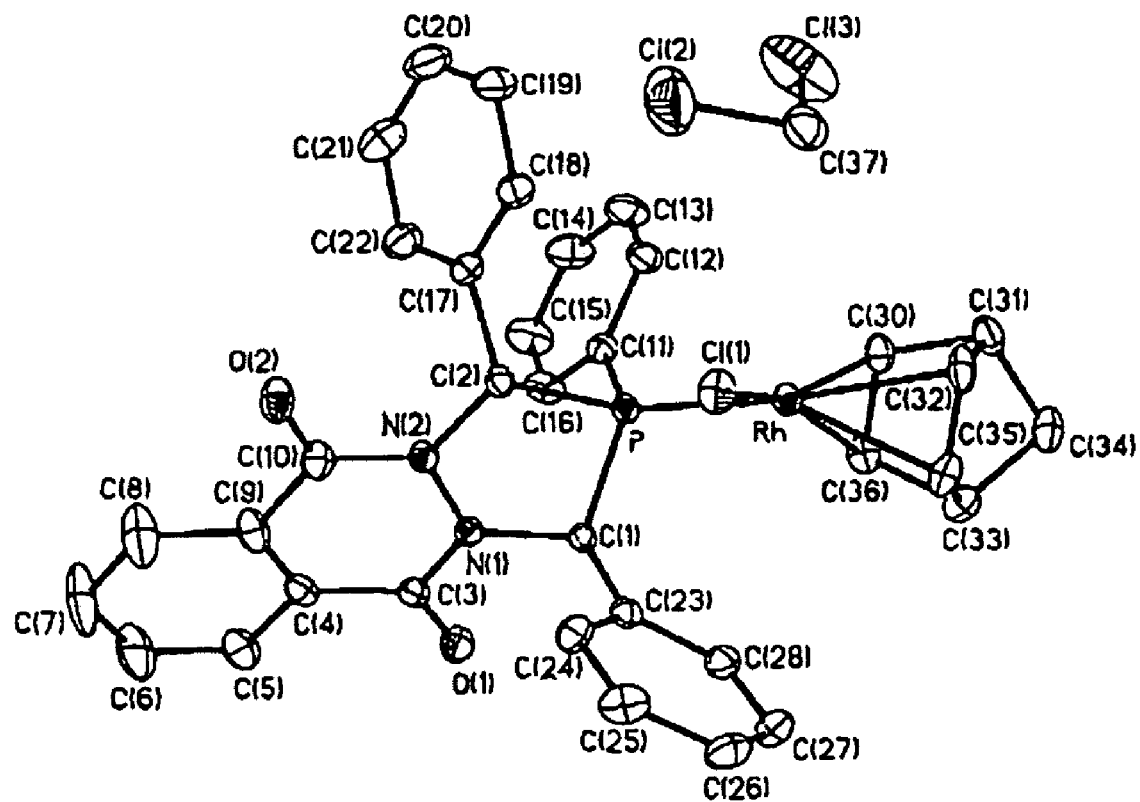
FIG. 16 is an X-ray crystal structure ORTEP diagram of a methylene chloride solvated Rh(NBD(Cl) complex with a diazaphospholane (6).

For example, excess diazaphospholanes 6a and 6b react with 1/2-[{Rh(NBD)Cl}$_2$] affording adducts with the formula [(6)Rh(NBD)Cl] in quantitative yields. Similarly, reaction of the N,N'-phthaloyl derivative of 9 with [(COD)Pt(CH$_3$)$_2$] in solution yields [(9-phthaloyl)Pt(CH$_3$)$_2$] in quantitative yield as judged by NMR spectroscopy and X-ray crystallography. X-ray crystallography was used to generate ORTEP diagrams of various metal complexes as seen in FIGS. 14, 15, and 16. $^1$H and $^{31}$P NMR spectra of various metal complexes are shown in FIGS. 7, and 9-13.

Standard reaction conditions known to those skilled in the art may be used to promote formation of the transition metal complex. For example, CO displacement may be promoted through the use of ultraviolet irradiation or by reaction with trimethylamine N-oxide as known by those skilled in the art.

Scheme 7 shows methods for preparing Rh(norbornadiene) complexes that include one or two diazaphosphacycles of the present invention.

Scheme 7

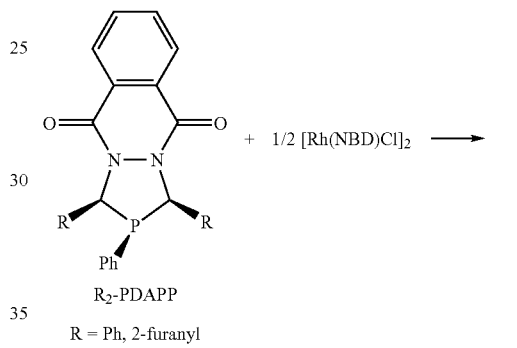

R$_2$-PDAPP

R = Ph, 2-furanyl

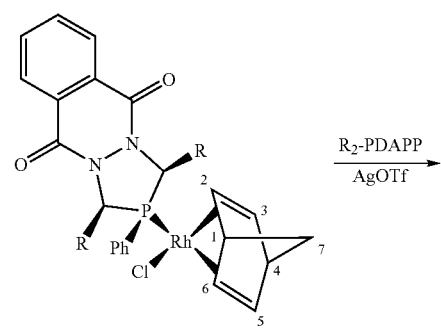

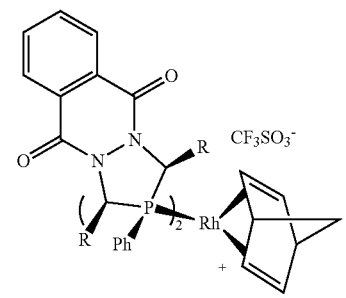

Scheme 8 shows various platinum complexes that have been synthesized using various diazaphosphacycles of the present invention Scheme 8
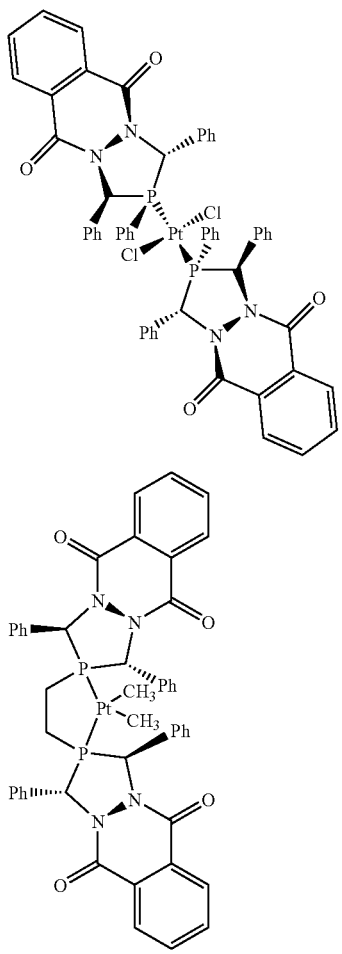
Scheme 9 shows various synthesized rhodium complexes that include the diazaphosphacycles of the present invention.
Scheme 9
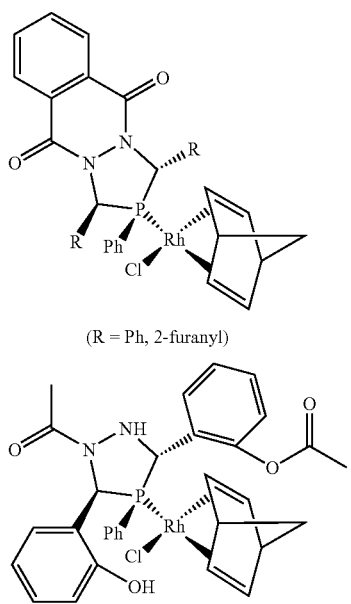
(R = Ph, 2-furanyl)
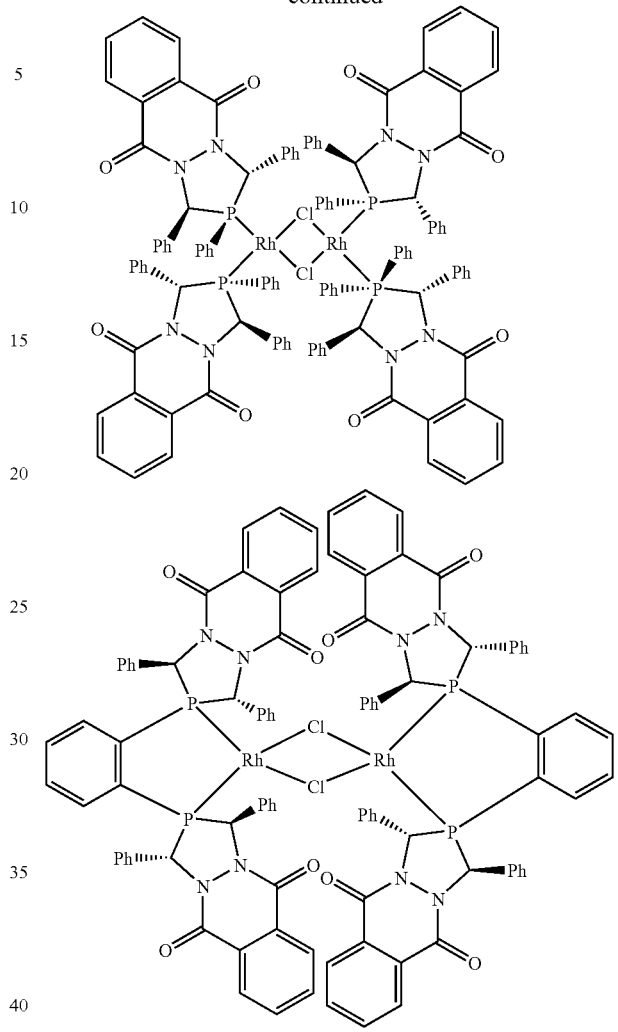
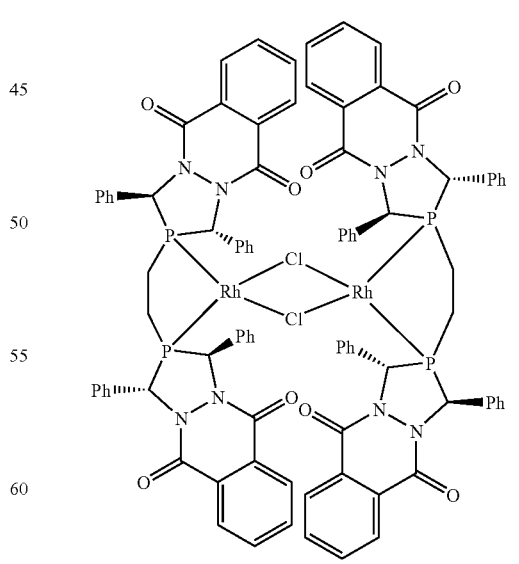
Scheme 10 shows a number of palladium complexes that have been synthesized using various diazaphosphacycles of the present invention.

Scheme 10

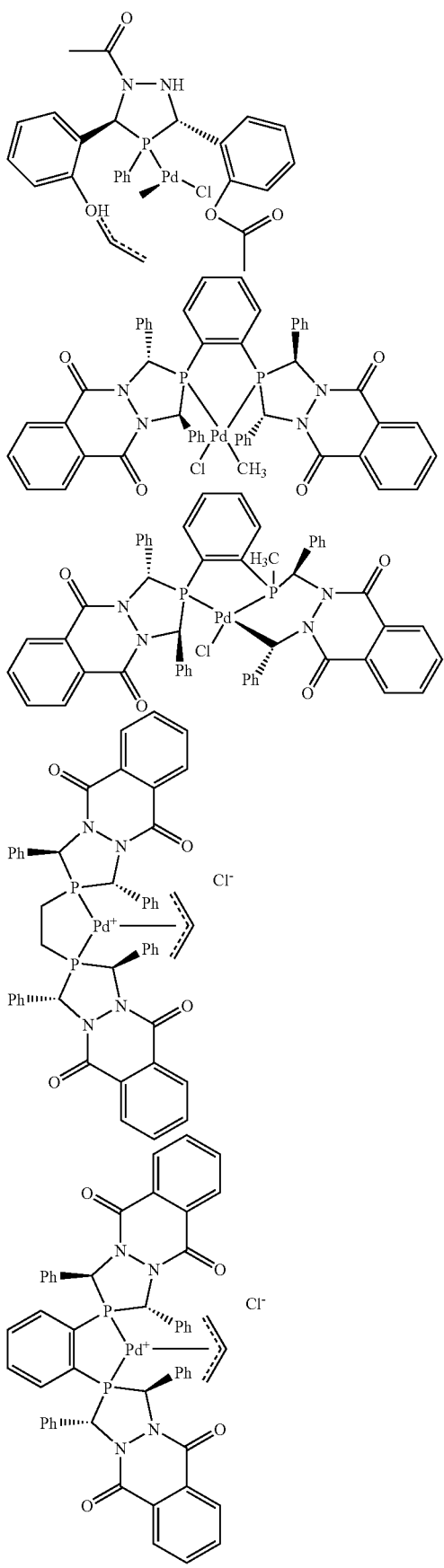

As noted above, there are many different types of reaction catalyzed by transition metal complexes. Examples of such reactions that may be catalyzed by the transition metal complexes of the present invention include, but are not limited to, alkene, alkyne, ketone, imine, oxime, aldehyde, nitrile, arene, carboxylic acid, ester, acid anhydride, and nitro group hydrogenations; hydrogenolysis reactions of alkyl halides, alkenyl halides, and acyl halides; hydrosilylation of alkenes, alkynes, ketones, and oximes; hydroboration of alkenes, alkynes, ketones, and oximes; hydroamination of alkenes and alkynes; hydroformylation of alkenes; hydroacylation of alkenes; hydrocarboxylation, hydroesterification, and hydrocarboxamidation of alkenes; carbonylation and double carbonylation of alkyl, aryl, and alkenyl halides; hydrocyanation of alkenes, dienes, and alkynes; alkene metathesis; cycloaddition of alkenes, dienes, and alkynes; cyclopropanation of alkenes; alkene and alkyne isomerization; Tischenko disproportionation of aldehydes; aziridination of alkenes; cross-coupling reactions; diborylation of alkanes; dehydrogenation of alkanes; allylic alkylation; allylic amination; allylic esterification; and amination and etherification of alkenyl and aryl halides. While each of the catalytic reactions is separately preferred, hydrogenation and hydroformylation reactions are particularly preferred transformations where transition metal complexes prepared from the diazaphosphacycles of the present invention may be utilized. Especially preferred catalytic transformations include those where enantioselectivity is desired.

As a general rule, 3,4-diazaphospholanes are bulky ligands. For example, the cone angle of 1a (172°) is comparable to that of tricyclohexylphosphine (170°). The bulkiness of the 3,4-diazaphosphacycles allows for the formation of transition metal complexes with crowded metal centers which may be associated with improved selectivity and/or activity during catalysis. Accordingly, diazaphosphacycles having cone angles greater than 170° are preferred.

EXAMPLES

General Considerations

Routine NMR characterization experiments, $^1$H NMR (300 and 500 MHz), $^{13}$C NMR (75.462 and 125.7 MHz), $^{19}$F NMR (282 MHz), and $^{31}$P NMR (121.49 and 202.4 MHz) were carried out on a Bruker AC-300 or a Varian 500 NMR spectrometer. $^1$H NMR data are reported as follows: chemical shift (multiplicity (b=broad, s=singlet, d=doublet, t=triplet, q=quartet, and m=multiplet), and integration). Chemical shifts for $^1$H NMR spectra are reported in ppm downfield from internal tetramethylsilane (TMS, δ scale) using residual protons in the deuterated solvents ($C_6D_6$, 7.15 ppm; $CDCl_3$, 7.25 ppm; and $CD_2Cl_2$, 5.31 ppm) as references. $^{13}$C and $^{31}$P NMR spectra were obtained using $^1$H decoupling, and the chemical shifts are reported in ppm vs. $Me_4Si$ ($CDCl_3$ at 77 ppm and $C_6D_6$ at 128 ppm) and 85% $H_3PO_4$ standard (external), respectively. Elemental analyses were provided by Desert Analysis (Phoenix, Ariz.).

$CDCl_3$ solvents were purchased from Aldrich Chemical (Milwaukee, Wis.), distilled over calcium hydride, and vacuum transferred into an air-tight solvent bulb prior to transfer into an inert-atmosphere glovebag. All reactions were carried out under a dry nitrogen atmosphere using standard Schlenk techniques unless otherwise noted.

Cyclohexyl phosphine and 1,2-bis(phosphino)ethane were purchased from Strem Chemicals, Inc. (Newburyport, Mass.) HCl (1.0 M in $Et_2O$ solution), succinyl chloride, phthaloyl chloride, and diethyl L-tartrate were purchased from Aldrich Chemical of Milwaukee, Wis. Acetyl chloride was purchased from J. T. Baker (Phillipsburg, N.J.).

The aryl azine derivatives (aryl-CH=N—N=CH-aryl) were prepared by reaction of the corresponding aldehyde (2 equiv.) with hydrazine under refluxing alcohol conditions. F. E. Hencoch, G. Hampton, C. R. Hauser, *J. Am. Chem. Soc.* 1969, 91, 676-681. The alkyl azine derivatives (alkyl-CH=N—N=CH-alkyl) (A. U. Blackham, N. L. Eatough, *J. Am. Chem. Soc.* 1962, 84, 2922-2930), phenylphosphine (R. C. Taylor, R. Kolodny, D. B. Walters, *Synthesis in Inorganic and Metal-Organic Chemistry* 1973, 3, 175-179), and o-bis(phosphino)benzene (E. P. Kyba, S.-T. Liu, R. L. Harris, *Organometallics* 1983, 2, 1877-1879) were prepared according to known literature methods. Phenylphosphine is commercially available from Aldrich Chemical (Milwaukee, Wis.).

General Synthesis for Compounds 1a-g and 5

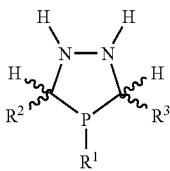

1a: $R^1$ = Ph; $R^2 = R^3$ = Ph
1b: $R^1$ = Ph; $R^2 = R^3$ = 2-furanyl
1c: $R^1$ = Ph; $R^2 = R^3$ = n-propyl
1d: $R^1$ = Ph; $R^2 = R^3$ = i-propyl
1e: $R^1$ = Ph; $R^2 = R^3$ = t-butyl
1f: $R^1$ = Cyclohexyl; $R^2 = R^3$ = Ph
1g: $R^1$ = Cyclohexyl; $R^2 = R^3$ = 2-furanyl

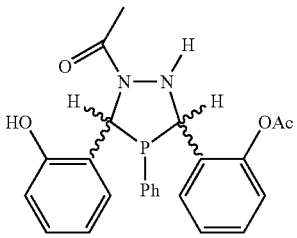

A diethyl ether (20 mL) solution of the appropriate azine derivative (4.55 mmol) was treated with HCl (ca. 4.75 mL, 4.75 mmol, 1.0 M in Et$_2$O solution) at 0° C. Immediately, a white solid precipitated from solution. Phenyl (or cyclohexyl for compounds 1f and 1g) phosphine (4.55 mmol) was added to this suspension at 0° C. and the reaction mixture was stirred for 4 hours (or overnight) at room temperature. Into the resultant white slurry was added a degassed 10% aqueous K$_2$CO$_3$ (ca 30 mL) solution at 0° C. The ether layer was separated via cannula, dried over MgSO$_4$, and filtered via cannula to obtain a colorless solution. The ether was evaporated under vacuum to yield the corresponding diazaphospholanes.

rac-1a: Yield=67% of a white solid (rac/meso=13). $^1$H NMR (CDCl$_3$): δ 4.53 (b, 2H, NH), 5.11 (d, $J_{H-P}$=22.1 Hz, 1H, PCHN), 5.54 (s, 1H, PCHN), 6.77 (m, 2H, Ph), 6.98 (m, 3H, Ph), 7.10-7.39 (m, 10H, Ph); $^{13}$C{$^1$H} NMR (CDCl$_3$): δ 71.51 (d, $J_{C-P}$=1.2 Hz, PCHN), 71.81 (d, $J_{C-P}$=5.7 Hz, PCHN), 126.29 (d, $J_{C-P}$=4.4 Hz, Ph), 126.37 (d, $J_{C-P}$=1.3 Hz), 127.30 (s), 127.41 (s), 127.86 (s), 128.15 (d, $J_{C-P}$=6.3 Hz), 128.94 (s), 128.98 (s), 133.34 (d, $J_{C-P}$=18 Hz), 134.53 (s), 141.10 (d, $J_{C-P}$=15.3 Hz), one quaternary carbon hasn't been assigned due to the overlap; $^{31}$P NMR (CDCl$_3$): δ 21.4 (d, $J_{P-H}$=23 Hz). Analysis calculated for C$_{20}$H$_{19}$N$_2$P: C, 75.46; H, 6.02; N, 8.8. Found: C, 74.85; H, 6.09; N, 8.8.

rac-1b: Yield=90% of a colorless oil (rac/meso=10). $^1$H NMR (CDCl$_3$): δ 4.0 (b, 1H, NH), 4.25 (b, 1H, NH), 4.84 (d, $J_{H-P}$=22.8 Hz, 1H. PCHN), 5.24 (d, $J_{H-P}$=2.2 Hz, 1H, PCHN), 5.63 (m, 1H, furan), 6.1 (dd, J=1.8, 3.3 Hz, 1H, furan), 6.31 (m, 1H, furan), 6.36 (m, 1H, furan), 7.12 (m, 1H, furan), 7.33 (m, 5H, Ph), 7.42 (m, 1H, furan); $^{13}$C{$^1$H} NMR (CDCl$_3$): δ 64.46 (d, J=20.3 Hz, PCHN), 65.55 (d, J=24.8 Hz, PCHN), 106.28 (d, J=3.2 Hz, furan), 107.13 (d, J=7 Hz, furan), 110.04 (s, furan), 110.55 (s, furan), 128.33 (d, J=7 Hz, Ph), 129.43 (s, Ph), 133.17 (d, J=18.5 Hz, Ph), 141.23 (s, furan), 142.62 (s, furan), 148 01 (furan), 150.09 (s, furan), 153.26 (d, J=14 Hz, Ph); $^{31}$P NMR (CDCl$_3$): δ 9.9 (d, $J_{P-H}$=23 Hz). Analysis calculated for C$_{16}$H$_{15}$O$_2$N$_2$P: C, 64.43; H. 5.07; N, 9.39. Found: C, 64.59; H, 5.14; N, 8.70.

rac-1c: Yield=>90% of a white solid (rac/meso=5). $^1$H NMR (CDCl$_3$): δ 0.82 (t, $J_{H-H}$=7.3 Hz, 3H, CH$_3$), 0.94 (t, $J_{H-H}$=7.3 Hz, 3H, CH$_3$), 1.3-1.7 (m, 8H, CH$_2$), 3.15 (doublet of triplet, $J_{H-H}$=7.0 Hz, $J_{P-H}$=16.2 Hz, 1H, CH), 3.94 (t, $J_{H-H}$=6.5 Hz, 1H, CH), 3.3-3.6 (b, 2H, NH) 7.34-7.41, (m, 3H, Ph), 7.47-7.55 (m, 2H, Ph); $^{13}$C{$^1$H} NMR (CDCl$_3$): δ 13.9 (s, CH$_3$), 21.5 (d, $J_{P-C}$=12.0 Hz), 22.0 (d, $J_{P-C}$=6.6 Hz), 37.0 (d, $J_{P-C}$=22.8 Hz), 67.0 (d, $J_{P-C}$=21.1 Hz, PCHN), CH (δ 67.3 (d, $J_{P-C}$=17.0 Hz, PCHN), 126.2 (d, $J_{P-C}$=6 Hz, C$_{meta}$), 127.0 (s, C$_{para}$), 133.8 (d, $J_{P-C}$=12 Hz, C$_{ortho}$), 136.8 (d, $J_{P-C}$=30 Hz, C$_{ipso}$); $^{31}$P NMR (CDCl$_3$): δ 1.1 (b). Analysis calculated for C$_{14}$H$_{23}$N$_2$P(hexane)$_{0.1}$: C, 67.72; H, 9.5; N, 10.82. Found: C, 68.12; H, 8.94; N, 10.72.

rac-1d: Yield=70% of a white solid with mainly a rac isomer. $^1$H NMR (CDCl$_3$): δ 0.9-1.13 (m, 13H, CH and CH$_3$), 1.94 (m, 1H, CH), 2.81 (dd, $J_{H-H}$=9.0 Hz, $J_{P-H}$=26.4 Hz, 1H, PCHN), 3.82 (dd, $J_{H-H}$=6.3 Hz, $J_{P-H}$=1.9 Hz, 1H, PCHN), 3.2-3.6, (b, 2H, NH), 7.34-7.41, (m, 3H, Ph), 7.47-7.55, (m, 2H, Ph); $^{13}$C{$^1$H} NMR(C$_6$D$_6$): δ 20.7, (d, $J_{C-P}$=13.7 Hz, CH$_3$), 21.4, (d, $J_{C-P}$=8.5 Hz, CH$_3$), 22.5 (d, $J_{C-P}$=4.8 Hz, CH$_3$), 23.5, (d, $J_{C-P}$=21.4 Hz, CH$_3$), 28.4 (s), 31.9 (d, $J_{C-P}$=20 Hz), 65.4 (d, $J_{C-P}$=18 Hz), 67.5 (d, $J_{C-P}$=32 Hz), 77.1 (d, $J_{C-P}$=18.1 Hz, PCHN), 128.6 (d, $J_{C-P}$=7 Hz, C$_{meta}$), 129.1 (s, C$_{para}$), 134.9 (d, $J_{C-P}$=19 Hz, C$_{ortho}$), 135.9 (d, $J_{C-P}$=26 Hz, C$_{ipso}$); $^{31}$P NMR (CDCl$_3$): δ −5.7 (d, $J_{P-H}$=2.4 Hz). Analysis calculated for C$_{14}$H$_{23}$N$_2$P(CH$_2$Cl$_2$)$_{0.1}$: C, 65.43; H, 9.04; N, 10.89. Found: C, 65.34; H, 8.61; N, 10.33.

rac-1e: Yield=61% of a white solid (rac/meso=6). $^1$H NMR (CDCl$_3$): δ 0.75 (d, $J_{H-P}$=1.1 Hz, 9H, CH$_3$), 1.04 (s, 9H, CH$_3$), 2.74 (d, $J_{H-P}$=21.3 Hz, PCHN), 3.81 (d, $J_{H-P}$=2.6 Hz, 1H, PCHN), 7.34 (m, 3H, Ph), 7.58 (m, 2H, Ph); $^{13}$C{$^1$H} NMR (CDCl$_3$): δ 28.11 (d, $J_{C-P}$=8.6 Hz, CH$_3$), 29.27 (d, $J_{C-P}$=4.9 Hz, CH$_3$), 33.05 (s, CCH$_3$), 33.78 (d, $J_{C-P}$=15.9 Hz, CCH$_3$), 79.54 (d, $J_{C-P}$=26.5 Hz, PCHN), 81.10 (d, $J_{C-P}$=19 Hz, PCHN), 128.55 (d, $J_{C-P}$=7.6 Hz, C$_{ortho}$), 129.31 (s, C$_{para}$), 135.13 (d, $J_{C-P}$=19.7 Hz, C$_{meta}$), 136.49 (d, $J_{C-P}$=25.4 Hz, C$_{ipso}$); $^{31}$P NMR (CDCl$_3$): δ−13.1 (d, $J_{P-H}$=19.8 Hz). Analysis calculated for C$_{16}$H$_{27}$N$_2$P: C, 69.03; H, 9.78; N, 10.06. Found: C, 69.3; H, 9.77; N, 9.91.

rac-1f: Yield=58% of a white solid with mainly a rac isomer. $^1$H NMR (CDCl$_3$): δ0.47 (m, 1H), 0.80 (m, 2H), 1.16-1.7 (m, 8H), 3.78 (b, 1H, NH), 4.14 (b, 1H, NH), 4.78 (s, 1H, PCHN), 4.85 (d, $J_{H-P}$=19.1 Hz, 1H, PCHN), 7.22-7.40 (m, 8H, Ph), 7.47-7.50 (m, 2H, Ph); $^{13}$C{$^1$H} NMR (CDCl$_3$): 26.2 (s), 26.3 (d, $J_{C-P}$=12.8 Hz), 26.9 (d, $J_{C-P}$=7.7 Hz), 29.0 (d, $J_{C-P}$=8.3 Hz), 30.7 (d, $J_{C-P}$=19.5 Hz), 32.2 (d, $J_{C-P}$=21.6 Hz,), 70.62 (d, $J_{C-P}$=3.2 Hz, PCHN), 71.0 (s, PCHN), 126.4 (d, $J_{C-P}$=3.2 Hz, Ph), 126.8 (s, Ph), 127.4 (d, $J_{C-P}$=1.3 Hz, Ph), 127.7 (d, $J_{C-P}$=9.5 Hz, Ph), 128.4 (s, Ph), 128.8 (s, Ph), 136.4 (s, CCH), 140.4 (d, $J_{C-P}$=15.9 Hz, CCH); $^{31}$P NMR (CDCl$_3$): δ11.68 (m). Analysis calculated for C$_{20}$H$_{25}$N$_2$P: C, 74.05; H, 7.77; N, 8.64. Found: C, 74.4; H, 8.11; N, 9.67.

rac-1g: Yield=61% of a white solid with mainly a rac isomer. $^1$H NMR (CDCl$_3$): δ 0.59 (m, 1H), 0.97 (m, 2H), 1.14-1.24 (m, 3H), 1.51-1.73 (m, 5H), 3.95 (b, 2H, NH), 4.74 (d, $J_{H-P}$=3.3 Hz, 1H, PCHN), 4.82 (d, $J_{H-P}$=22.8 Hz, PCHN), 6.23 (m, 1H), 6.29-6.35 (m, 3H), 7.37-7.39 (m, 2H); $^{13}$C{$^1$H} NMR (CDCl$_3$): δ26.21 (s, CH$_2$), 26.47 (d, $J_{C-P}$=12.1 Hz), 26.75 (d, $J_{C-P}$=8.3 Hz), 29.25 (d, $J_{C-P}$=10.2 Hz), 30.35 (d, $J_{C-P}$=19.1 Hz), 33.07 (d, $J_{C-P}$=30.0 Hz), 64.29 (d, $J_{C-P}$=28.6 Hz, PCHN), 65.0 (d, $J_{C-P}$=23.5 Hz, PCHN), 106.54 (d, $J_{C-P}$=2.6 Hz, furan), 107.25 (d, $J_{C-P}$=7.0 Hz, furan), 110.36 (s, furan), 110.63 (s, furan), 141.56 (s, furan), 142.52 (s, furan), 149.65 (s, PCCH), 153.11 (d, $J_{C-P}$=20.4 Hz, PCCH), $^{31}$P NMR (CDCl$_3$): δ 15.6 (d, $J_{P-H}$=21.3 Hz). Analysis calculated for C$_{16}$H$_{21}$N$_2$O$_2$P: C, 63.15; H, 6.96; N, 9.2. Found: C, 63.26; H, 7.11; N, 9.25.

rac-5: Yield=79% of the crude product. X-ray quality crystals were grown from CH$_2$Cl$_2$/hexanes at room temperature. $^1$H NMR (CDCl$_3$): δ 2.50 (s, 3H, CH$_3$), 2.51 (s, 3H, CH$_3$), 5.04 (d, J=8.8 Hz, 1H, NH), 5.53 (dd, J=17.3, 8.8, Hz, 1H, PCHN), 6.32 (d, J=2.6 Hz, 1H, PCHN), 6.85-7.20 (m, 11H, Ph), 7.28 (m, 1H, Ph), 7.43 (m, 1H. Ph), 9.50 (b, 1H. OH); $^{13}$C{$^1$H} NMR (CDCl$_3$): δ 21.45 (s, CH$_3$), 21.77 (s, CH$_3$), 58.07 (d, $J_{C-P}$=19.7 Hz, PCHN), 61.40 (d, $J_{C-P}$=28.61 Hz, PCHN), 146.34 (s, Ph), 156.67 (d, $J_{C-P}$=5.5 Hz, Ph), 168.96 (s, CO), 171.17 (s, CO); Peaks at 118-135 ppm have not been assigned due to the complexity. $^{31}$P NMR (CDCl$_3$): δ 14.6 (m). Analysis calculated for C$_{24}$H$_{23}$N$_2$O$_4$P(CH$_2$Cl$_2$)$_{0.25}$: C, 63.92; H, 5.2; N, 6.15. Found: C, 64.27; H, 4.96; N, 6.41.

Synthesis of Compounds 2a and 2b

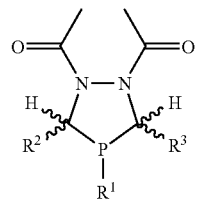

2

2a: R$^1$ = Ph; R$^2$ = R$^3$ = 2-furanyl
2b: R$^1$ = Cyclohexyl; R$^2$ = R$^3$ = 2-furanyl The appropriate azine (1.55 mmol) in Et$_2$O (50 mL) was treated with acetyl chloride (15.5 mmol, 10 equiv.) at 0° C. The appropriate phosphine (phenylphosphine (2a); cyclohexylphosphine (2b)) (1.55 mmol) was then slowly added at 0° C., and the mixture stirred at room temperature overnight. To the resultant white slurry was added 10% aqueous K$_2$CO$_3$ (ca. 20 mL) at 0° C. For 2a, the aqueous and organic layers were filtered off via cannula to obtain a white solid which was then washed with distilled water and Et$_2$O. X-Ray quality crystals were obtained from CH$_2$Cl$_2$ and hexane at room temperature. For 2b, the ether layer was separated, dried over MgSO$_4$, and filtered off via cannula to obtain a colorless solution. The ether was then removed under reduced pressure to yield the corresponding diazaphospholane.

rac-2a: Yield=80% with a white solid With a mainly rac isomer. $^1$H NMR(CDCl$_3$): δ 1.71 (s, 3H, CH$_3$), 2.21 (s, 3H, CH$_3$), 5.9 (dd, J=3.3, 1.8 Hz, 1H, furan), 6.03 (d, J=3.3 Hz, 1H, furan), 6.30 (dd, J=3.3, 1.8. Hz, 1H, furan), 6.44 (d, J=3.3 Hz, 1H, furan), 6.55 (d, $J_{H-P}$=23.2 Hz, 1H, NCHP), 6.72 (d, $J_{H-P}$=3.3 Hz, NCHP), 6.74 (m, 1H, furan), 7.11-7.22 (m, 5H, Ph), 7.39 (m, 1H, furan); $^{13}$C{$^1$H} NMR (CDCl$_3$): δ 19.08 (s, CH$_3$), 20.68 (s, CH$_3$), 52.72 (d, $J_{C-P}$=19.7 Hz, NCHP), 56.75 (d, $J_{C-P}$=31.2 Hz, NCHP), 108.24 (d, $J_{C-P}$=2.5 Hz, furan), 109.91 (s, furan), 110.53 (d, $J_{C-P}$=10.2 Hz, furan), 110.83 (s, furan), 128.03 (d, $J_{C-P}$=7.0 Hz, C$_{meta}$), 129.38 (s, C$_{para}$), 132.51 (d, $J_{C-P}$=20.3 Hz, C$_{ortho}$), 141.86 (s, furan), 143.51 (s, furan), 150.21 (d, $J_{C-P}$=32.4 Hz, C$_{ipso}$), 171.80 (s, CO), 174.75 (s, CO), two carbons are not assigned probably due to the overlap; $^{31}$P NMR (CDCl$_3$): δ23.5 (d, $J_{P-H}$=22.9 Hz). Analysis calculated for C$_{20}$H$_{19}$N$_2$O$_4$P: C, 62.83; H, 5.01; N, 7.33. Found: C, 62.91; H, 4.65; N. 7.21.

rac-2b: Yield=25% a white solid with mainly a rac isomer. $^1$H NMR (CDCl$_3$): δ0.43 (m, 1H), 0.75-1.0 (m, 2H), 1.1-1.3 (m, 3H), 1.5-1.8 (m, 5H), 1.68 (s, 3H, CH$_3$), 2.22 (s, 3H, CH$_3$), 6.2-6.4 (m, 6H, furan and PCHN), 7.3-7.4 (m, 2H, furan); $^{13}$C{$^1$H} NMR (CDCl$_3$): δ 19.42 (s, CH$_3$), 20.50 (s, CH$_3$), 26.00 (s), 26.29 (d, $J_{C-P}$=2.6 Hz), 26.44 (d, $J_{C-P}$=5.1 Hz), 29.13 (d, $J_{C-P}$=19.1 Hz), 29.88 (d, $J_{C-P}$=12.8 Hz), 32.39 (d, $J_{C-P}$=19.1 Hz), 52.83 (d, $J_{C-P}$=22.9 Hz, PCHN), 54.29 (d, $J_{C-P}$=33.1 Hz, PCHN), 108.80 (s, furan), 110.27 (d, $J_{C-P}$=9.5 Hz, furan), 110.72 (s, furan), 110.88 (s, furan), 142.15 (s, furan), 143.14 (s, furan), 149.56 (d, $J_{C-P}$=3.2 Hz, furan), 150.75 (d, $J_{C-P}$=26.71 Hz, furan), 173.15 (s, CO), 174.77 (s, CO); $^{31}$P NMR (CDCl$_3$): δ27.0 (m). Analysis calculated for C$_{20}$H$_{25}$N$_2$O$_4$P: C, 61.85; H, 6.49; N, 7.21. Found: C, 62.18, H, 6.79; N, 7.30.

Synthesis of Compounds 3, 4, and 6

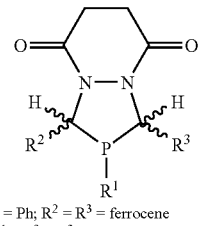

3 and 4

3: R$^1$ = Ph; R$^2$ = R$^3$ = ferrocene
4a: R$^1$ = R$^2$ = R$^3$ = Ph
4b: R$^1$ = cyclohexyl; R$^2$ = R$^3$ = 2-furanyl

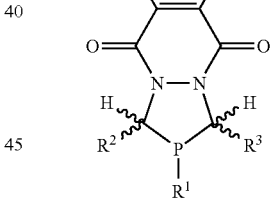

6

6a: R$^1$ = R$^2$ = R$^3$ = Ph
6b: R$^1$ = Ph; R$^2$ = R$^3$ = 2-furanyl
6c: R$^1$ = Ph; R$^2$ = R$^3$ = o-tolyl
6d: R$^1$ = Ph; R$^2$ = R$^3$ = 2-naphthyl
6e: R$^1$ = Ph; R$^2$ = R$^3$ = C$_6$F$_5$
6f: R$^1$ = Ph; R$^2$ = R$^3$ = n-propyl
6g: R$^1$ = Ph; R$^2$ = R$^3$ = i-propyl The appropriate azine (1.55 mmol) in Et$_2$O (50 mL) was treated with the diacid dichloride (4.65 mmol, 3 equiv.) at 0° C. The phosphine (1.55 mmol) was then slowly added at 0° C., and the mixture was stirred at room temperature overnight. To the resultant white slurry was added a 10% aqueous K$_2$CO$_3$ solution (ca. 20 mL) at ice-bath temperature. For 3, 4, 6a, 6b, and 6d, the aqueous and organic layers were filtered off via cannula to obtain a white solid. Subsequently, the product was washed with distilled water and Et$_2$O, and the residue was dried in vacuo to obtain an analytically pure product. For 6c, 6e, 6f and 6g, the ether layer was separated, dried over MgSO$_4$, and filtered off by cannula yielding the corresponding ether solution. The ether was removed in vacuo to obtain the desired product. Compounds 6 can also be made from the addition of corresponding compound 1 into a THF solution of phthaloyl chloride (3 equivalents) at ice-bath temperature. The mixture was stirred overnight at room temperature, placed under reduced pressure, washed with $Et_2O$ and degassed water, and dried overnight to yield the corresponding compound 6.

meso-3: Yield=69% of a reddish brown solid (rac/meso=0.6). X-ray quality crystals of meso-3 were grown from $CH_2Cl_2$/hexane at room temperature. $^1$H NMR ($CDCl_3$): δ 2.50-2.6 (m, 2H, $CH_2$), 2.65-2.77 (m, 2H, $CH_2$), 3.88 (m, 2H, Cp), 4.0 (m, 2H, Cp), 4.04 (m, 2H), 4.14 (s, Cp, 10H) 4.30 (m, 2H, Cp), 6.04 (s, 2H, CHN), 7.45 (m, 5H, Ph); $^{13}$C{$^1$H} NMR ($CDCl_3$): δ 29.3 (s, $CH_2$), 59.4 (d, $J_{C-P}$=24.2 Hz, PCHN), 67.73 (s, CH), 68.12 (s CH), 68.62 (d, $J_{C-P}$=10.8 Hz, PCHN), 69.1 (s, Cp), 70.4 (d, $J_{C-P}$=3.8 Hz, CH), 85.05 (d, $J_{C-P}$=19.7 Hz, CCH), 129.2 (d, $J_{C-P}$=6.4 Hz, $C_{meta}$), 129.94 (s, $C_{para}$), 130.8 (d, JCP=15.8 Hz, $C_{ortho}$), 134.2 (d, $J_{C-P}$=23.5 Hz, $C_{ipso}$), 165.2 (s, CO); $^{31}$P NMR ($CDCl_3$): δ3.0 (s). Analysis calculated for $C_{32}H_{29}N_2O_2Fe_2P(CH_2Cl_2)_{0.5}$ C, 59.63; H, 4.55; N, 4.21; Found: C, 60.19 (61.10); H, 4.60 (4.37); N, 4.36 (4.36).

rac-4a: Yield=95% of the crude product with mainly a rac isomer. X-ray quality crystals were grown from $CH_2Cl_2$/hexanes at room temperature. $^1$H NMR ($CDCl_3$): δ 2.83 (m, 4H, $CH_2$) 5.82 (d, $J_{H-P}$=19.1 Hz, 1H, PCHN), 6.51 (s, 1H, PCHN), 6.71-6.75 (m, 2H, Ph), 6.9-7.05 (m, 5H, Ph), 7.1-7.2 (m, 2H,Ph), 7.25-7.30 (m, 1H, Ph), 7.30-7.38 (m, 3H, Ph), 7.42-7.46 (m, 2H, Ph); $^{13}$C NMR ($CDCl_3$): δ29.46 (s, $CH_3$), 30.38 (s, $CH_3$), 57.14 (d, $J_{C-P}$=21.0 Hz, PCHN), 61.72 (d, $J_{C-P}$=31.8 Hz, PCHN), 124.79 (d, $J_{C-Pb}$=1.9 Hz, Ph), 125.41 (d, $J_{C-P}$=8.3 Hz, Ph), 126.57 (s, Ph), 127.85 (s, Ph), 128.10 (d, $J_{C-P}$=6.4 Hz, Ph), 129.07 (s, Ph), 129.72 (s, Ph), 130.15 (d, $J_{C-P}$=24.2 Hz, Ph), 132.20 (d, $J_{C-P}$=19.0 Hz, Ph), 133.53 (s, Ph), 137.10 (d, $J_{C-P}$=15.3 Hz, Ph), 165.24 (s, CO), 167.71 (s, CO), one peak is not assigned due to the overlap; $^{31}$P NMR ($CDCl_3$): δ11.6 (m). Analysis calculated for $C_{24}H_{21}N_2O_2P$: C, 71.99; H, 5.29;

N, 7.0. Found: C, 71.21; H, 5.29; N. 6.96.

rac-4-b: Yield=59% of the crude product with mainly a rac isomer. X-Ray quality crystals were grown from $CH_2Cl_2$/hexanes at room temperature. $^1$H NMR ($CDCl_3$): δ0.75 (m, 1H), 1.0 (m, 2H), 1.25 (m, 3H), 1.6 (m, 3H), 1.8 (m, 2H), 2.6-2.7 (m, 4H), 5.86 (d, $J_{H-P}$=14.8 Hz, 1H, PCHN), 5.96 (s, PCHN), 6.26 (m, 1H, furan), 6.33 (d, $J_{H-P}$=1.5 Hz, 1H, furan), 6.36 (dd, $J_{H-P}$=1.9, 3.3 Hz, 1H, furan), 7.35 (m, 2H, furan); $^{13}$C{$^1$H} NMR ($CDCl_3$): δ 25.80 (d, $J_{C-P}$=1.3 Hz), 26.51 (s), 26.47 (d, $J_{C-P}$=20.3 Hz), 28.49 (d, $J_{C-P}$=7 Hz), 29.47 (s), 29.76 (d, $J_{C-P}$=22.9 Hz), 30.33 (s), 32.47 (d, $J_{C-P}$=21. Hz), 50.25 (d, $J_{C-P}$=24.2 Hz), 54.65 (d, $J_{C-P}$=31.2 Hz), 107.16 (d, $J_{C-P}$=2.5 Hz), 107.76 (d, $J_{C-P}$=7 Hz), 110.62 (s), 110.94 (s), 141.73 (d, $J_{C-P}$=1.3 Hz), 142.97 (s), 147.45 (d, $J_{C-P}$=2.5 Hz), 150.21 (d, $J_{C-P}$=17.2 Hz), 165.55 (s, CO), 167.59 (s, CO); $^{31}$P NMR ($CDCl_3$): δ12.9 (m). Analysis calculated for $C_{20}H_{23}N_2O_4P$: C, 62.17; H, 6.0; N, 7.25. Found: C, 62.04; H, 5.52; N, 7.16.

rac-6a: Yield=65% of a white solid with a rac isomer. X-ray quality crystals from grown from $CH_2Cl_2$/hexanes at room temperature. $^1$H NMR ($CDCl_3$): δ 6.25 (d, 1H, J(H,P)=19.5 Hz, PCHN), 6.95 (s, 1H, PCHN), 7.05 (m, 3H, Ph), 7.13-7.19 (m, 5H, Ph), 7.3-7.4 (m, 7H, Ph), 7.3-7.8 (m, 2H, Ph), 8.44 (m, 1H, CH), 8.48 (m, 1H, CH), $^{13}$C{$^1$H} NMR ($CDCl_3$): δ 60.3 (d, $J_{C-P}$=19.7 Hz, PCHN), 64.9 (d, $J_{C-P}$=31.8 Hz, PCHN), 125.10 (d, $J_{C-P}$=3.2 Hz), 125.42 (d, $J_{C-P}$=6.3 Hz), 126.88 (d, $J_{C-P}$=1.9 Hz), 127.83 (s), 127.94 (s), 128.06 (d, $J_{C-P}$=2.6 Hz), 128.55 (d, $J_{C-P}$=7.0 Hz), 129.33 (d, $J_{C-P}$=1.3 Hz), 129.43 (s), 130.03 (s), 130.22 (s), 130.35 (s), 130.46 (s), 132.85 (d, $J_{C-P}$=1.2 Hz), 132.93 9s), 133.188 (s), 133.55 (d, $J_{C-P}$=8.3 Hz), 137.2 (d, $J_{C-P}$=14.6 Hz), 156.30 (s, CO), 156.50 (s, CO); $^{31}$P NMR ($CDCl_3$): δ–1.3 (m). Analysis calculated for $C_{28}H_{21}N_2O_2P$: C, 74.99; H, 4.72; N, 6.25. Found: C, 75.21; H, 4.64; N. 6.32.

rac-6b: Yield=71% of a white solid with mainly a rac isomer. X-ray quality crystals were grown from $CH_2Cl_2$/hexanes at room temperature. $^1$H NMR ($CDCl_3$): δ 5.81 (m, 1H, furan), 6.09 (dd, J=3, 2 Hz, 1H, furan), 6.32 (m, 1H furan), 6.44 (m, 1H, furan), 6.47 (d, $J_{H-P}$=28 Hz, 1H, PCHN), 6.73 (d, $J_{H-P}$=2 Hz, 1H, PCHN), 6.92 (m, 1H, furan), 7.3 (m, 5H, Ph), 7.35 (m, 1H, furan), 7.77 (m, 2H, CH), 8.22 (m, 1H, CH), 8.36 (m, 1H, CH); $^{13}$C{$^1$H} NMR ($CDCl_3$): δ 54.7 (d, $J_{C-P}$=18 Hz, PCHN), 60.2 (d, $J_{C-P}$=30 Hz, PCHN), 107.2 (d, $J_{C-P}$=4 Hz, furan), 108.1 (d, $J_{C-P}$=6 Hz, furan), 110.5 (s, furan), 110.8 (s, furan), 127.7 (s, CH), 127.8 (s, CH), 128.6 (d, $J_{C-P}$=8 Hz, Ph), 129.3 (s, CC=O), 130.2 (d, $J_{C-P}$=22 Hz, $C_{ipso}$), 130.5 (S, CC=O), 130.8 (s, Ph), 133.1 (s, CH), 133.3 (d, $J_{C-P}$=10 Hz, Ph), 133.5 (s, CH), 141.6 (s, furan), 143.3 (s, furan), 145.8 (s, furan), 149.2 (d, $J_{C-P}$=13 Hz, furan), 156.3 (s, 2C, C=O); $^{31}$P NMR ($CDCl_3$): δ–14.7 (b). Analysis calculated for $C_{24}H_{17}N_2O_4P$: C, 67.29; H, 4.0; N, 6.54. Found: C, 66.99; H, 3.76; N, 6.39.

rac-6c: Yield=28% of a white solid (rac/meso=11). $^1$H NMR ($CDCl_3$): δ2.46 (s, 3H, $CH_3$), 2.47 (s, 3H, $CH_3$), 5.98 (d, J=9.3 Hz, 1H), 6.35 (d, $J_{H-P}$=18 Hz, 1H, PCHN), 6.48 (t, J=7 Hz, 1H), 6.79 (d, J=7.5 Hz, 1H), 6.90 (s, 1H, PCHN), 6.85-7.3 (m, 10H), 7.84 (m$^{-2}$H, CH), 8.29 (m, 1H, CH), 8.39 (m, 1H, CH), How many H's; $^{13}$C{$^1$H} NMR (CDCl3): δ 20.4 (d, $J_{C-P}$=4 Hz, $CH_3$), 20.6 (d, $J_{C-P}$=7 Hz, $CH_3$), 59.0 (d, $J_{C-P}$=20 Hz, PCHN), 62.8 (d, $J_{C-P}$=32 Hz, PCHN), Peaks at 120-140 ppm have not been assigned due to the complexity; $^{31}$P NMR ($CDCl_3$): δ –13.9 (d, $J_{P-H}$=17 Hz). Analysis calculated for $C_{30}H_{25}N_2O_2P(CH_2Cl_2)_{0.5}$: C, 70.59; H, 5.05; N, 5.40. Found: C, 70.93; H. 4.93; N, 5.42 rac-6d: Yield (isolated)=24% of a white solid (rac/meso=11). $^1$H NMR ($CDCl_3$): δ6.41 (d, $J_{H-P}$=19 Hz, 1H, PCHN), 7.07 (s, 1H, PCHN), 8.30 (m, 1H, CH), 8.46 (m, 1H, CH), 7.0-8.0 (m, 22H); $^{13}$C{$^1$H} NMR ($CDCl_3$): δ 61.2 (d, $J_{C-P}$=21 Hz, PCHN), 65.9 (d, $J_{C-P}$=31 Hz, PCHN), Peaks at 120-140 ppm have not been assigned due to the complexity; $^{31}$P NMR ($CDCl_3$): δ –2.6 (d, $J_{P-H}$=19 Hz). Analysis calculated for $C_{36}H_{25}N_2O_2P$: C, 78.82; H, 4.59; N, 5.11. Found: C, 78.21; H, 4.59; N, 5.19.

rac-6e: Yield=90% of a yellow solid (rac/meso=2). Recrystallization from hexane gave the pure rac isomer (38%) and X-ray quality crystals of rac-6e were obtained from slow evaporation of a hexane solution. $^1$H NMR ($CDCl_3$): δ 6.65 (d, $J_{H-P}$=19.1 Hz, 1H, PCHN), 6.91 (d, $J_{H-P}$=4.1 Hz, 1H, PCHN), 7.3–7.4 (m, 5H, Ph), 7.8 (m, 2H), 8.28 (m, 1H, CH), 8.34 (m, 1H); $^{13}$C{$^1$H} NMR ($CDCl_3$): δ51.89 (d, $J_{C-P}$=22.3 Hz, PCHN), 57.01 (d, $J_{C-P}$=33.7 Hz, PCHN), 156.42 (s, CO), 156.58 (s, CO), peaks at 110-145 ppm have not been assigned due to the complexity. $^{31}$P NMR ($CDCl_3$): δ –2.7 (m). Analysis calculated for $C_{28}H_{11}N_2F_{10}O_2P$: C, 53.52; H, 1.76; N, 4.46. Found: C, 53.72; H, 2.01; N, 4.23.

rac-6f: Yield=80% of a yellow oil (rac/meso=4). $^1$H NMR ($CDCl_3$): δ 0.75 (t, $J_{H-H}$=7 Hz, 3H $CH_3$), 0.92 (t, $J_{H-H}$=7 Hz, 3H, $CH_3$), 1.5 (m, 4H, $CH_2$), 1.7 (m, 2H, $CH_2$), 1.9 (m, 2H, $CH_2$), 4.86 (ddd, $J_{H-P}$=21 Hz, $J_{H-H}$=12, 4 Hz, 1H, PCHN), 5.30 (dd, $J_{H-H}$=9, 5 Hz, 1H, PCHN), 7.25-7.6 (m, 5H, aromatics), 7.6-8.1 (m, 2H, aromatics), 8.31 (m, 2H, aromatics); $^{13}$C NMR ($CDCl_3$): δ14.4 (s, $CH_3$), 20.8 (d, $J_{C-P}$=10 Hz, $CH_2$), 21.4 (d, $J_{C-P}$=8 Hz, $CH_2$), 35.6 (s, $CH_2$), 35.8 (s, $CH_2$), 59.9 (d, $J_{C-P}$=17 Hz, PCHN), 62.9 (d, $J_{C-P}$=27 Hz, PCHN), 128.0 (s), 128.3 (s), 129.6 (d, $J_{C-P}$=8 Hz), 131.6 (s), 134.0 (d, $J_{C-P}$=12 Hz), 134.9 (s), 135.1 (s), A range of 120-140 ppm has not been assigned due to the complexity; $^{31}$P NMR (CDCl$_3$): δ −18.9 (b). Analysis calculated for C$_{22}$H$_{25}$N$_2$O$_2$P: C, 69.46; H, 6.62; N, 7.36. Found: C, 66.13; H, 4.96; N, 3.66.

rac-6g: Yield=49.9% of a white solid, prepared from the treatment of 1d and phthaloyl chloride in THF. $^1$H NMR (CDCl$_3$): δ 0.41, (d, J$_{H-H}$=7.1 Hz, 3H, CH$_3$), 0.95-1.06 (m, 9H, OH$_3$) 2.41, (oct, J$_{H-H}$=6.8 Hz, 1H, CHMe$_2$), 3.13, (oct, J$_{H-H}$=6.9 Hz, 1H, CHMe$_2$), 4.94 (dd, J$_{H-H}$=5.8 Hz, J$_{P-H}$=20.4 Hz, 1H, PCHN), 5.32 (dd, J$_{H-H}$=6.2 Hz, J$_{P-H}$=1.7 Hz, 1H, PCHN), 7.30-7.45, (m, 3H), 7.60-7.68, (m, 2H), 7.79-7.89, (m, 2H), 8.30-8.44, (m, 2H); $^{13}$C{$^1$H} NMR (CDCl$_3$): δ18.0 (d, J$_{P-C}$=1.0 Hz, CH$_3$), 18.7 (d, J$_{P-C}$=10.0 Hz, CH$_3$), 19.8, (d J$_{P-C}$=8.86 Hz, CH$_3$), 20.2 (d, J$_{P-C}$=10.0 Hz, CH$_3$), 22.5 (d, J$_{P-C}$=4.8 Hz, CH$_3$), 23.5 (d, J$_{P-C}$=21.4 Hz, CH$_3$), 65.7 (d, J$_{P-C}$=17.6 Hz, PCHN), 67.8 d, J$_{P-C}$=32.0 Hz, PCHN), 157.6 (s, CO), 156.7 (s, CO); peaks at 127.4-135.1 ppm have not been assigned due to the complexity. $^{31}$P NMR (CDCl$_3$): δ −25.7. Analysis calculated for C$_{22}$H$_{25}$N$_2$O$_2$P: C, 69.46; H, 6.62; N, 7.36. Found: C, 69.45; H, 6.31; N, 7.42.

General Synthesis of Compounds 7 and 9

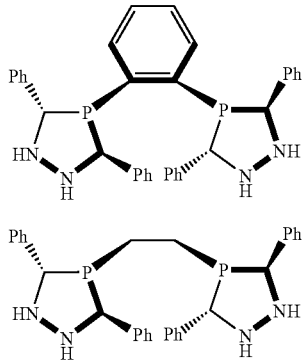

Phenyl azine (322.4 mg, 1.55 mmol) in Et$_2$O (50 mL) was treated with HCl (0.78 mL, 2M Et$_2$O solution) at 0° C. The corresponding bis-phosphine (1,2-diphosphinobenzene (7); 1,2-diphosphinoethane (9)) (0.775 mmol) was then slowly added at 0° C., and the mixture was stirred at room temperature overnight. To the resultant white slurry was added a 10% aqueous K$_2$CO$_3$ solution (ca. 20 mL) at ice-bath temperature. The aqueous and organic layers were filtered off via cannula to obtain a white solid which was subsequently washed with distilled water and Et$_2$O. The white solid was dried overnight under vacuum to obtain analytically pure compound 7. X-ray quality crystals for rac-7 were grown from CH$_2$Cl$_2$ and hexanes at room temperature.

rac-7: Yield=32% of a white solid. $^1$H NMR (CDCl$_3$): δ 3.75 (dd, J$_{H-H}$=6.6, 10.3 Hz, 2H, NH), 4.34 (t, J$_{H-H}$=11.4 Hz, 2H, NH), 4.55 (d, J$_{H-H}$=6.3 Hz, 2H, PCHN), 4.71 (q, J=11.7, 2H, PCHN), 6.63 (m, 4H), 6.80 (m, 4H), 6.94 (m, 2H), 7.23-7.40 (m, 14H); $^{13}$C{$^1$H} NMR (CDCl$_3$): δ 70.40 (t, J$_{C-P}$=6.4 Hz, PCHN), 71.27 (t, J$_{C-P}$=14.0 Hz, PCHN), 126.40 (t, J$_{C-P}$=2.5 Hz), 126.58 (s), 127.47 (s), 128.75 (s), 129.24 (s), 131.72 (s), 134.98 (s), 141.08 (t, J$_{C-P}$=8.3 Hz), 141.5 (s). Peaks at 127-128 ppm haven't been assigned due to the complexity. $^{31}$P NMR (CDCl$_3$): δ 11.6 (t, Jp-H=10.7 Hz). Analysis calculated for C$_{34}$H$_{32}$N$_4$P$_2$: C, 73.11; H, 5.77; N, 10.03. Found: C, 73.05; H, 5.74; N, 10.1.

rac-9: Yield=32% of a white solid. $^1$H NMR (CDCl$_3$): δ 0.95 (m, 4H, CH2), 3.76 (dd, J$_{H-H}$=7.0, 11.0 Hz, 2H, NH), 4.11 (t, J=10.3 Hz, 2H, NH), 4.41 (d, J$_{H-H}$=7.0 Hz, 2H, PCHN), 4.82 (q, J=10.3 Hz, 2H, PCHN), 7.28-7.40 (m, 6H, Ph), 7.50 (m, 4H, Ph); $^{13}$C{$^1$H} NMR (CDCl$_3$): δ 19.8 (d, J$_{C-P}$=7 Hz, CH$_2$P), 69.7 (dd, J$_{C-P}$=10.8, 14 Hz, PCHN), 73.3 (t, J$_{C-P}$=11.4 Hz, PCHN), 126.1 (s), 126.7 (s), 127.44 (s), 127.6 (d, J$_{C-P}$=11 Hz), 128.57 (s), 128.83 (s), 136.4 (s, C$_{ipso}$), 139.9 (t, J$_{C-P}$=8.3 Hz, C$_{ipso}$); $^{31}$P NMR (CDCl$_3$): δ15.8 (m). Analysis calculated for C$_{30}$H$_{32}$N$_4$P$_2$: C, 70.58; H, 6.32; N, 10.97. Found: C, 70.29; H, 6.31; N, 11.0.

Synthesis of rac-8 Compound

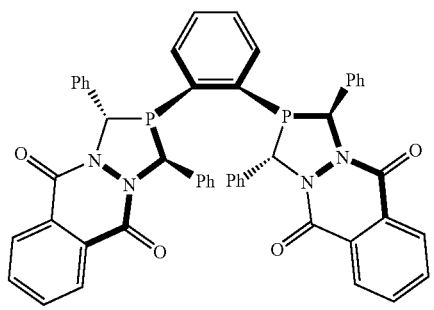

1,2-Bis(phosphino)benzene (0.2 mL, 1.55 mmol) was added to the ether solution of phenyl azine (648 mg, 3.1 mmol) and phthalolyl chloride (0.9 mL, 6.25 mmol) at 0° C. After the mixture stirred over night, an aqueous 10% K$_2$CO$_3$ solution (30 mL) was added into the resultant white slurry at ice-bath temperature. The aqueous and ether layers were removed via cannula and the residue dried in vacuo. The residue was washed with THF and Et$_2$O (1:1 (v/v)) to obtain a white solid of rac-8 in a 23% yield. X-ray quality crystals were grown from CH$_2$Cl$_2$/hexanes at room temperature. In addition, rac-8 was made from the addition of rac-7 to phthaloyl chloride in THF at 0° C. $^1$H NMR (CDCl$_3$): δ 6.15 (t, J$_{P-H}$=10.3 Hz, 2H, PCHN), 6.18 (s, 2H, PCHN), 6.96 (m, 4H), 7.1 (m, 4H), 7.17 (m, 2H), 7.3-7.4 (m, 14H), 7.8 (m, 4H), 8.2 (m, 2H, CH), 8.36 (m, 2H, CH); $^{13}$C{$^1$H} NMR (CDCl$_3$): S 60.56 (s, PCHN), 65.75 (t, J$_{C-P}$=18.5 Hz, PCHN), 156.86 (s, CO), 157.11 (s, CO), Peaks at 125-140 ppm haven't been assigned due to the complexity; 31p NMR (CDCl$_3$): δ−14.4 (t, J$_{P-H}$=10.7 Hz). Analysis calculated for C$_{50}$H$_{36}$N$_4$O$_4$P$_2$ (CH$_2$Cl$_2$)$_{0.8}$: C, 68.81; H, 4.27; N, 6.32. Found: C, 68.55; H, 4.37; N, 6.14.

Resolution Procedure for Tartaric Acid Derivatives: Tart-1a, Tart-1e, and Tart-9

Di-O-methyl-tartaric acid was prepared according to the literature method. I. Felner, K. Schenker, *Helv. Chim. Acta.* 1970, 53, 4, 754-762. The acid was converted to the acid chloride based loosely on literature procedure. T. Purdie, C. R. Young, *J. Chem. Soc.* 1910, 1532. The acid was slowly added to a slight excess of PCl$_5$ in benzene at 0° C. under nitrogen followed by stirring overnight. The resulting solution was filtered and solvent was removed in vacuo to yield a yellow solid. The solid was purified by sublimation. $^1$H NMR (CDCl$_3$): 3.57 (s, 6H), 4.73 (s, 2H); $^{13}$C {$^1$H} NMR (CDCl$_3$): δ 60.5, 87.4, 169.3.

A THF solution of the acid chloride was added dropwise to a stirring THF solution of the diazaphospholane at room temperature. After stirring overnight, the THF was removed in vacuo. Ether was added to the resulting oil, and to the resulting solution was added aqueous 10% K$_2$CO$_3$. The ether layer was dried over MgSO$_4$, and the ether was removed in vacuo. Resolution of the Tart-9 diastereomers was accomplished on Aldrich silica preparative TLC plates (20 cm×20 cm×1 mm) with a mobile phase of ethyl acetate/hexane. Both diastereomers were separately recovered. Resolution of Tart-1a and Tart-1e was accomplished by flash chromatography using a column packed with Silica Gel 60 (EM Science) and eluents of 15:1 and 30:1 $CH_2Cl_2$/ethyl acetate. One diastereomer of each was cleanly recovered. The other diastereomers each had unidentified impurities in $^1H$ and $^{31}P$ NMR's. Absolute configurations of the resolved diastereomers are not currently known.

Tart-9: [Crude product has only 2 peaks in $^{31}P$ NMR] $(R_f=0.17)$: $^1H$ NMR $(CDCl_3)$: 0.95 (m, 4H, $CH_2$), 3.61 (s, 6H, $OCH_3$), 3.75 (s, 6H, $OCH_3$), 3.89 (d, $J_{H-H}$=12 Hz, 2H, $CHOCH_3$), 4.27 (d, $J_{H-H}$=12 Hz, 2H, $CHOCH_3$), 5.56 (s, 2H, PCHN), 5.56 (d, $J_{H-P}$=16 Hz, 2H, PCHN), 6.9-7.4 (m, 30H); $^{31}P$ NMR $(CDCl_3)$: $\delta$ 4.7 (m); $(R_f=0.28)$: $^1H$ NMR $(CDCl_3)$: 3.41 (s, 6H, $OCH_3$), 3.61 (s, 6H, $OCH_3$), 3.88 (d, $J_{H-H}$=3 Hz, 2H, $CHOCH_3$), 3.97 (d, $J_{H-H}$=3 Hz, 2H, $CHOCH_3$), 5.42 (d, $J_{H-P}$=17 Hz, 2H, PCHN), 5.57 (s, 2H, PCHN), 6.9-7.4 (m, 30H); $^{31}P$ NMR $(CDCl_3)$: $\delta$3.5 (m).

Tart-1a: [Crude product has two diastereomers as main products with several unidentified impurities] $(R_f=0.33)$: $^1H$ NMR $(CDCl_3)$: 3.58 (s, 3H, $OCH_3$), 3.71 (s, 3H, $OCH_3$), 3.97 (d, $J_{H-H}$=12 Hz, 1H, $CHOCH_3$), 4.17 (d, $J_{H-H}$=12 Hz, 1H. $CHOCH_3$), 5.80 (d, $J_{H-P}$=19 Hz, 1H, PCHN), 6.38 (s, 1H, PCHN), 6.6-7.4 (m, 15H); $^{31}P$ NMR $(CDCl_3)$: $\delta$ 9.2 (m) with a trace of other impurities; $R_f=0.55$): $^1H$ NMR $(CDCl_3)$: 3.47 (s, 3H, $OCH_3$), 3.57 (s, 3H, $OCH_3$), 3.86 (d, $J_{H-H}$=4 Hz, 1H, $CHOCH_3$), 4.00 (d, $J_{H-H}$=4 Hz, 1H, $CHOCH_3$), 5.71 (d, $J_{H-P}$=19 Hz, 1H, PCHN), 6.42 (s, 1H, PCHN), 6.6-7.5 (m, 15H); $^{31}P$ NMR $(CDCl_3)$: $\delta$ 8.5 (m).

Tart-1e: [Crude product has two diastereomers as main products with several unidentified impurities] $(R_f=0.31)$: $^1H$ NMR $(CDCl_3)$: 0.84 (d, $J_{H-P}$=1 Hz, 9H, $C(CH_3)_3$), 0.98 (s, 9H, $C(CH_3)_3$), 3.51 (s, 3H, $OCH_3$), 3.53 (s, 3H, $OCH_3$), 3.86 (d, $J_{H-H}$=3 Hz, 1H, $CHOCH_3$), 3.94 (d, $J_{H-H}$=3 Hz, 1H, $CHOCH_3$), 4.58 (d, $J_{H-P}$=21 Hz, 1H, PCHN), 4.74 (d, $J_{H-P}$=3 Hz, 1H, PCHN), 7.2-7.7 (m, 5H); $^{31}P$ NMR $(CDCl_3)$: $\delta$1.4; $(R_f=0.15)$: $^1H$ NMR $(CDCl_3)$: 0.78 (d, $J_{H-P}$=1 Hz, 9H, $C(CH_3)_3$), 0.96 (s, 9H, $C(CH_3)_3$), 3.68 (s, 3H, $OCH_3$), 3.72 (s, 3H, $OCH_3$), 3.99 (d, $J_{H-H}$=11 Hz, 1H, $CHOCH_3$), 4.25 (d, $J_{H-H}$=11 Hz, 1H, $CHOCH_3$), 4.53 (d, $J_{H-P}$=21 Hz, 1H, PCHN), 4.81 (d, $J_{H-P}$=3 Hz, PCHN), 7.2-7.7 (m, 5H); $^{31}P$ NMR $(CDCl_3)$: $\delta$ 4.8 plus one impurity with peak height ratio bout 5:1 product to impurity at $\delta$ -6.2.

Reaction of an Acid Dichloride with a Diimine

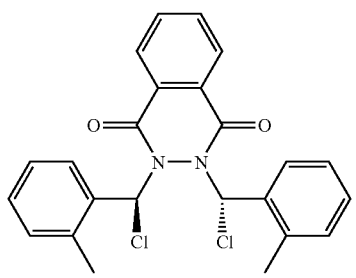

All manipulations were performed under a $N_2$ atmosphere and using standard Schlenk techniques.

Two equivalents of phthaloyl dichloride were added dropwise to a stirred ether solution of the azine (970 mg) formed by the reaction of equivalents of 2-methyl benzaldehyde with hydrazine. After stirring overnight, the solution was set aside. After 5 days, 100 mg of crystals had formed which were characterized using X-ray crystallographic analysis.

Synthesis of Diazaphospholane from Dichloro Compound

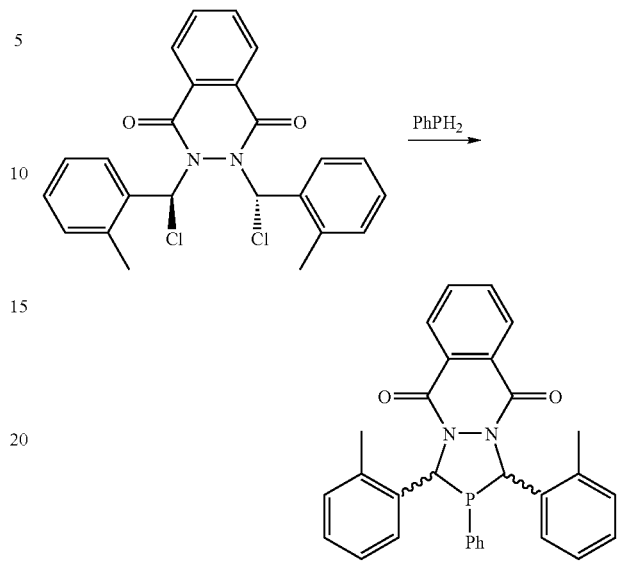

All manipulations were performed under $N_2$ using standard Schlenk techniques.

A solution of the azine (383 mg in 100 mL $Et_2O$) prepared from 2-methyl benzaldehyde and hydrazine was treated with 2 equivalents of phthaloyl dichloride and stirred overnight. Phenylphosphine (170 mg) was lowly added, and the solution was stirred overnight. To the resultant solution as added a 10% aqueous solution of $K_2CO_3$. The ether layer was separated, dried over $MgSO_4$, and filtered using a glass frit. The ether was removed, and 400 mg of the diazaphospholane was obtained as a 10:1 rac:meso mixture.

Synthesis of Diimine from trans-1,2-Diaminocyclohexane and 2-Naphthaldehyde

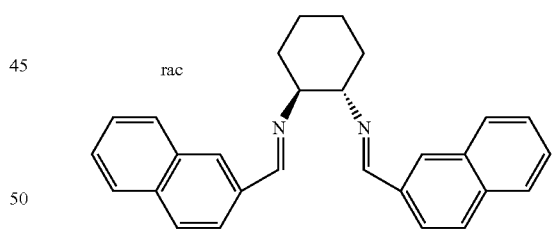

Trans-1,2-diaminocyclohexane (2.0 mL) was added dropwise to a stirred solution of two equivalents of 2-naphtaldehyde (8.2 g in 100 mL benzene). After stirring for one hour, the solution was heated to 50° C. for 30 minutes. The solvent was removed on a rotary evaporator. The resulting solid was redissolved in benzene and was then removed by rotary evaporation to azeotropically remove water. This procedure was repeated once more. The remaining solid was rinsed eight times with 25 mL of ether and filtered. The remaining solid was dried under vacuum for 15 minutes and was used without further purification (yield=5.17 g).

Synthesis of Diazaphosphacycle from Diimine formed from trans-1,2-Diaminocyclohexane and 2-Naphthaldehyde

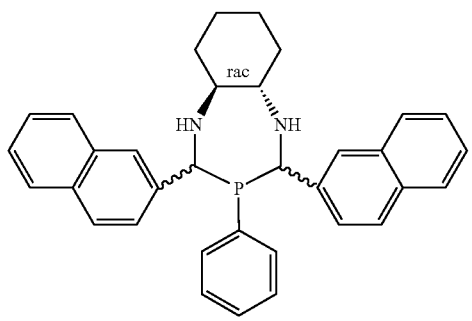

All manipulations were performed under $N_2$ using standard Schlenk techniques

Phenyl phosphine (0.3 mL) was added dropwise to a stirred solution of the diimine formed from trans-1,2-diaminocyclohexane and benzaldehyde (1.06 g in 100 mL THF). After 10 minutes, an HCl solution (1.36 mL of a 2M solution in ether) was added dropwise. The resulting solution was then stirred for 18 hours. THF was removed under vacuum and 75 mL of ether was added. A 10% aqueous solution of $K_2CO_3$ was added to the ether mixture and was stirred until all solid had gone into solution. The ether layer was separated, dried over $MgSO_4$, and filtered. The ether was then removed under vacuum to yield a solid product (crude yield=1.31 g) consisting of two diastereomers. $^{31}P$ NMR ($CDCl_3$): δ 19, 9.

Synthesis of an $\eta^3$-allyl Pd Complex with a Bidentate Diazaphospholane

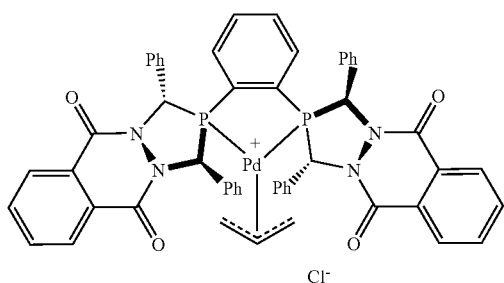

To a Teflon® brand fluorinated polymer capped NMR tube was added [($\eta^3$-$C_3H_5$)PdCl]$_2$ (5.2 μmol) (Aldrich Chemical (Milwaukee, Wis.)) and the diazaphospholane (10.3 μmol) indicated in the above structure. $CD_2Cl_2$ ca 1 mL) was added, and the NMR tube was agitated until the solids went into solution. The designated Pd complex was obtained and characterized by NMR. $^1H$ NMR ($CD_2Cl_2$): δ 3.4 (allyl $CH_2$), 4.9 (allyl CH), 6.4 (PCHN), 6.6-7.6 (unassigned), 7.9 (phthaloyl), 8.3 (phthaloyl); $^{31}P$ NMR: δ 71 ppm.

Synthesis of a Dimethyl Pt Complex with a Bidentate Diazaphospholane

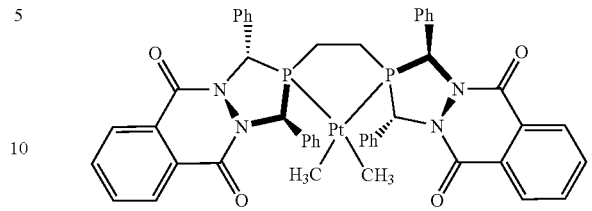

To a Teflon® brand fluorinated polymer capped NMR tube was added, [(cyclooctadiene)Pt(CH$_3$)$_2$] (1.3 μmol) (Aldrich Chemical (Milwaukee, Wis.) and the diazaphospholane (1.2 μmol) indicated by the above structure. Approximately 1 mL of $C_6D_6$ was added and the NMR tube was agitated until the solids went into solution. The solution was evaporated to dryness in vacuo to remove free cyclooctadiene, and approximately 1 mL of $C_6D_6$ was added. The dimethyl Pt complex indicated above was characterized by NMR. $^1H$ NMR($C_6D_6$): δ 0.6 ($CH_3$), 0.2-1.6 (broad ethyl peaks unassigned), 5.8 (PCHN), 6.6 (PCHN), 6.7-7.4 (aromatics), 8.4 (phthaloyl); $^{31}P$ NMR: δ 63 (with $^{195}$Pt satellites; $J_{Pt\text{-}P}$=1680 Hz).

Synthesis of Rhodium(diazaphospholane)Cl(norbornadiene)

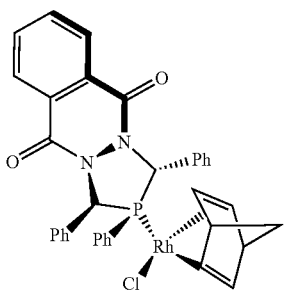

A $CH_2Cl_2$ solution of 2,5-diphenyldiazaphospholane (100 mg, 0.224 mmol) was added into a $CH_2Cl_2$ solution of [Rh(norbornadiene)Cl]$_2$ (51.7 mg, 0.112 mmol) at room temperature. The resulting mixture was stirred for 1 hour and pumped on under vacuum to quantitatively yield a red-orange solid. X-ray quality crystals were obtained from $CH_2Cl_2$ and hexane at room temperature. The Rh complex indicated above was characterized by X-ray crystallography and NMR spectroscopy. $^1H$ NMR ($CDCl_3$): δ 1.33 (s, 2H), 3.04 (m 1H), 3.34 (m, 1H), 3.50 (m, 1H), 3.60 (m, 1H), 5.09 (m, 1H), 5.22 (m, 1H), 6.9-7.0 (m, 5H), 7.1-7.43 (m, 9H), 7.50 (m, 3H), 7.79 (m, 5H), 8.24 (m, 1H), 8.32 (m, 1H); $^{31}P\{^1H\}$ NMR ($CDCl_3$): δ 45.0 (d, $J_{Rh\text{-}P}$=189 Hz).

Synthesis of [{1,2-bis(diazaphospholanes)benzene}RhCl]$_2$

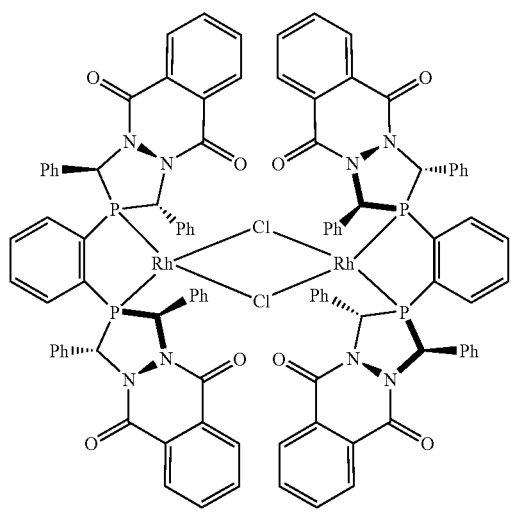

A CH$_2$Cl$_2$ solution of 1,2-bis(diazaphospholanes)benzene as, indicated in the above structure was added into a [Rh(norbornadiene)Cl]$_2$ (prepared according to known procedure see E. W. Abel, M. A. Bennet, G. Wilkinson, J. Chem. Soc. 1959, 3178-3182 and available from Aldrich Chemical (Milwaukee, Wis.)) (or [Rh(COD)Cl]$_2$) (prepared according to known procedure see G. Giordano, R. H. Crabtree, Inorg. Synth. 1990, 28 88-90 and available from Strem Chemicals, Inc. (Newburyport, Mass.)) solution in CH$_2$Cl$_2$ at room temperature. The reaction mixture was stirred for 1 hour and pumped on under vacuum to quantitatively yield a red-orange solid. X-ray quality crystals were obtained from CH$_2$Cl$_2$ and hexane at room temperature. The dirhodium complex indicated above was characterized by X-ray crystallography and NMR spectroscopy. $^1$H NMR (CDCl$_3$): δ 5.71 (br, 2H), 6.16 (s, 2H), 7.1-7.3 (m, 14H), 7.47 (m, 6H), 7.88 (m, 4H), 8.32 (m, 2H), 8.40 (m, 2H); $^{31}$P{$^1$H} NMR (CDCl$_3$): δ 87.7 (d, J$_{Rh-P}$=209 Hz).

Synthesis of {Rhodium[1,2-bis(diazaphospholanes)benzene](COD)}BF$_4$

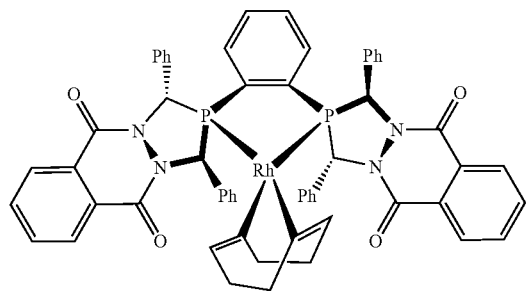

A 1:1 mixture of [Rh(COD)$_2$]BF$_4$ (prepared according to known procedure see T. G. Schenck, J. M. Downes, C. R. Miline, P. B. Mackenzie, M. Boucher, J. Wheland, B. Bosnich, Inorg. Chem. 1985, 24 2334-2337 and available from Pressure Chemical Co. (Pittsburgh, Pa.)) and 1,2-bis(diazaphospholanes)benzene was prepared in an NMR tube at room temperature. After CDCl$_3$ was added, the mixture was agitated well. $^{31}$P{$^1$H} NMR indicated that the initial product was Rh[bis(diazaphospholanes)benzene](COD))BF$_4$ showing a resonance signal at 62.2 ppm (J$_{Rh-P}$=163 Hz). After 2 days, a new resonance signal appeared at 87.7 ppm (J$_{Rh-P}$=209 Hz), which was identified as [{1,2-bis(diazaphospholanes)benzene}RhCl]$_2$ Catalytic Allylic Alkylation

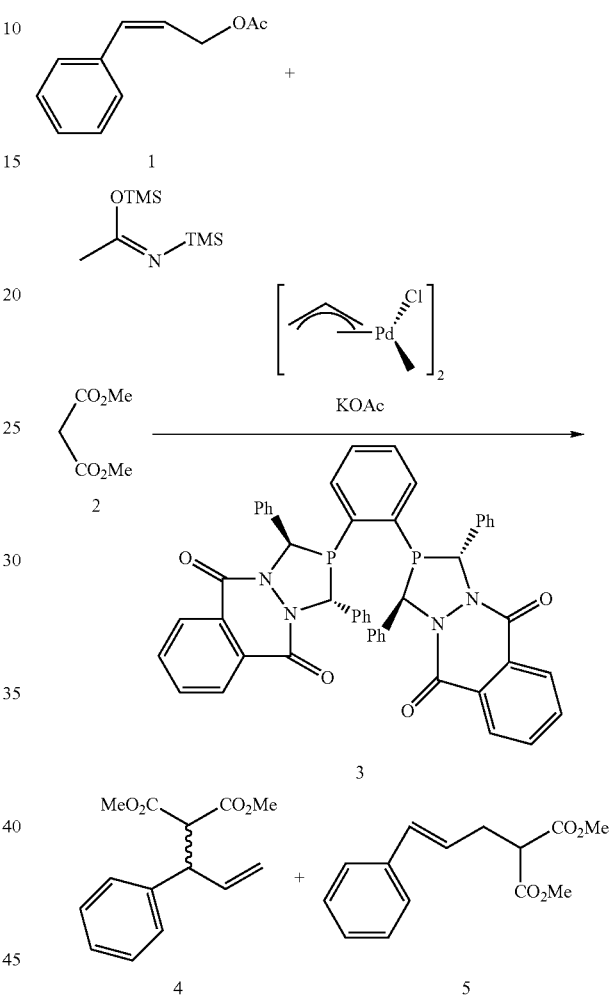

For the purposes of this example, the numbers refer to the numbers of the compounds in the reaction scheme presented above except as otherwise noted.

All manipulations were performed under a N$_2$ atmosphere.

A vial was prepared with 2.8 mg of [Pd(η$^3$-C$_3$H$_5$)Cl]$_2$ (Aldrich Chemical Milwaukee, Wis.)) and 15.0 mg of the diazaphospholane (3) (Example 8) in 1 mL CH$_2$Cl$_2$. A second vial was prepared with 1.0 mmol of cinnamyl acetate (1), 3.0 mmol of dimethyl malonate (2), 3.0 mmol of N,O-bis(trimethylsilyl)acetamide $_2$ (Aldrich Chemical (Milwaukee, Wis.)), and two grains of potassium acetate in 1 mL of CH$_2$Cl$_2$. The second vial was added to the first vial and the solution was stirred for 18 hours at ambient temperature. The solvent was removed under vacuum and the $^1$H NMR of the product dissolved in CDCl$_3$ was taken. As determined by NMR, the conversion of cinnamyl acetate to alkylated products 4 and 5 was >98% with a 33:1 ratio of 5:4.

Hydrogenation of Methylacetamidoacrylate

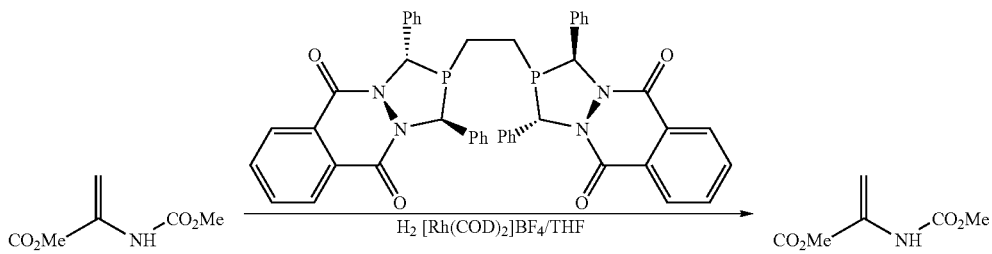

Figure 8:
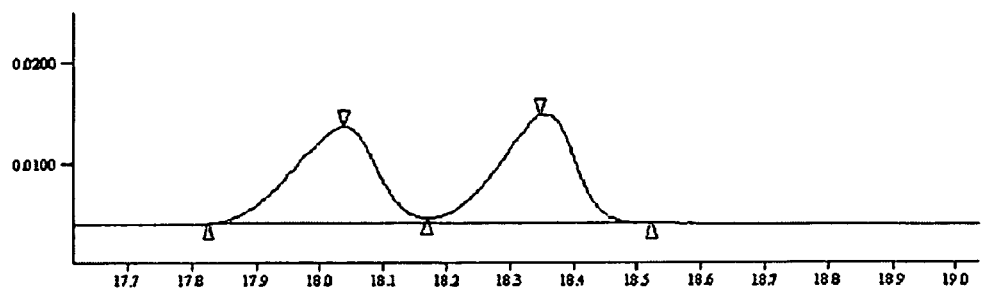
FIG. 8 is a GC spectrum for the hydrogenation product of the hydrogenation of methylacetamidoacrylate using a chiral column with a racemic mixture of the catalyst with a Rh diazaphosphacycle complex.
Figure 9:
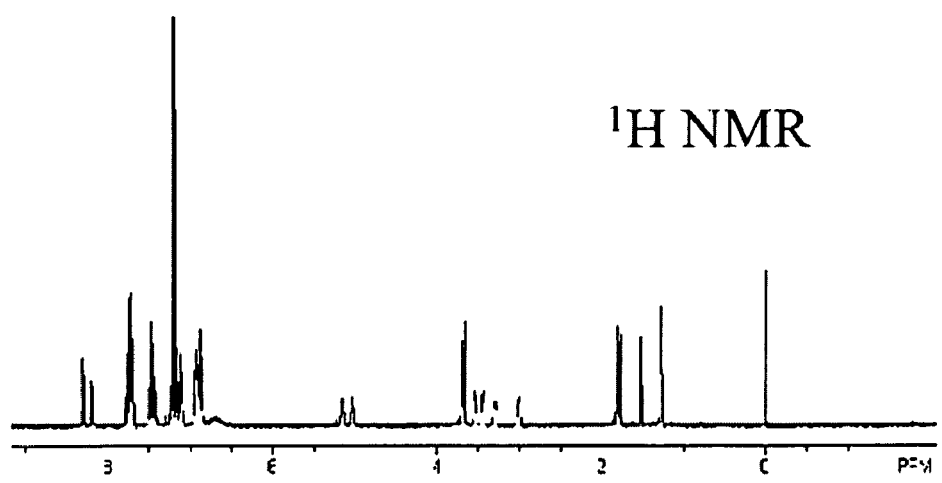
Figure 10:
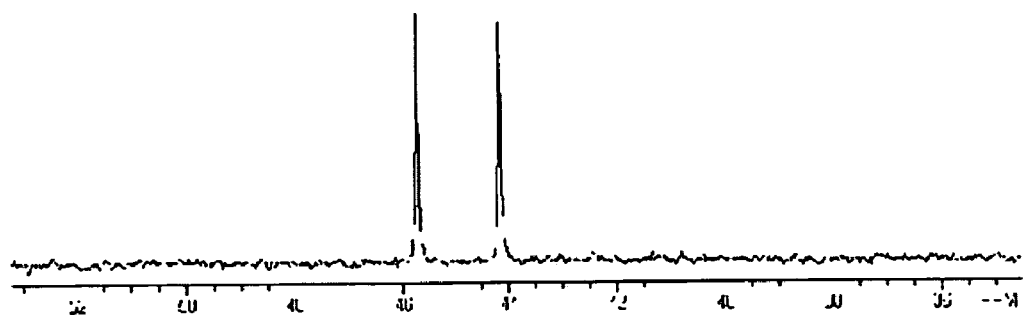
Figure 11:
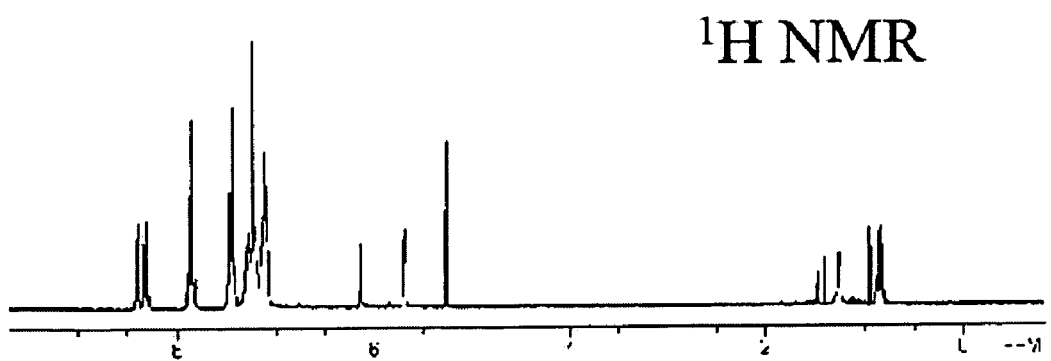
FIG. 11 is a $^{1}H$ NMR spectrum of [{1,2-bis(diazaphospholanes)benzene}RhCl]$_2$ where the 1,2-bis(diazaphospholane)benzene is compound 8.
Figure 12:
FIG. 12 is a $^{31}P$ NMR spectrum ($^{1}H$ coupled) of [{1,2-bis(diazaphospholanes)benzene}RhCl]$_2$ where the 1,2-bis(diazaphospholane)benzene is compound 8.
Figure 13:
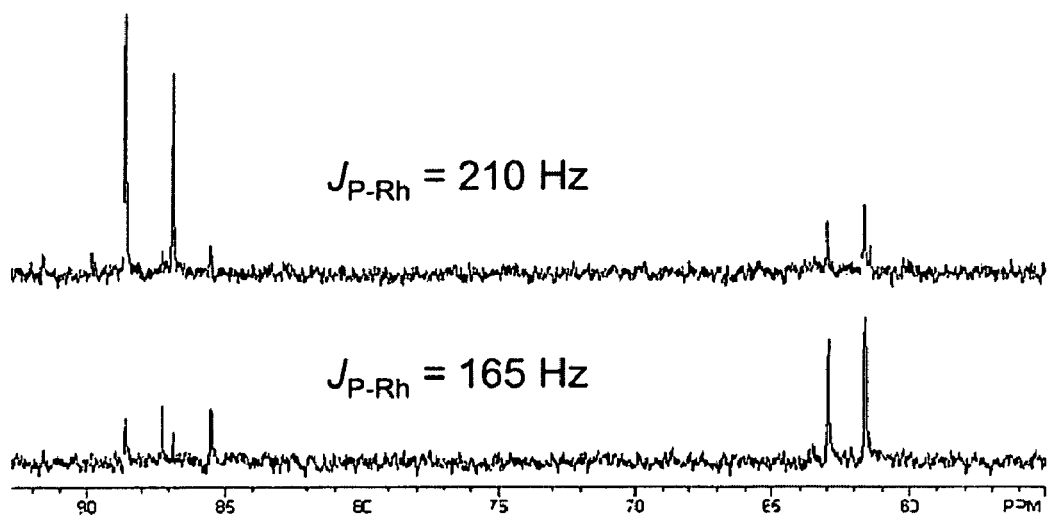
FIG. 13 is a stacked NMR spectrum comparing the $^{31}P$ NMR spectrum of [{1,2-bis(diazaphospholanes)benzene}RhCl]$_2$ (top) with that of {Rhodium[1,2-bis(diazaphospholanes)benzene](COD)}BF$_4$ (bottom) where the 1,2-bis(diazaphospholane)benzene is compound 8.

Under a $N_2$ atmosphere, a mixture of 1,2-bis(diazaphospholane)ethane 3.85 mg, 0.005 mmol) and [Rh(COD)$_2$]BF$_4$ (2 mg, 0.005 mmol) 2 (Pressure Chemical Co. (Pittsburgh, Pa.)) in THF (3 mL) was stirred for 1 hour at room temperature. Next, methylacetamidoacrylate (14.3 mg, 0.1 mmol)$_2$ (Sigma-Aldrich (St. Louis, Mo.)) in THF (3 mL) was added and hydrogen (H$_2$) bubbled for 30 minutes at room temperature. The reaction flask was then sealed and stirred overnight. The reaction was then filtered through a short path of silica gel (150 mg) and washed with CH$_2$Cl$_2$ (5 mL). The hydrogenated product with complete conversion was identified using GC chromatography (FIG. 8) which shows the hydrogenation product of the hydrogenation using a chiral GC column with a racemic mixture of the catalyst.

All references cited herein are specifically incorporated by reference into the disclosure of this application.

It is understood that the invention is not limited to the embodiments set forth herein for illustration, but embraces all such forms thereof as come within the scope of the claims.

What is claimed is:

1. A method for synthesizing a transition metal complex, comprising, reacting a diazaphosphacycle of formula III with a starting transition metal complex to provide the transition metal complex, wherein the phosphorous atom of the diazaphosphacycle is bonded to the transition metal and the diazaphosphacycle of formula III has the following structure

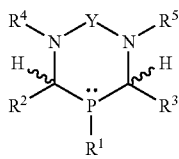

wherein

R$^1$ is selected from the group consisting of substituted and unsubstituted aryl groups, substituted and unsubstituted alkyl groups, substituted and unsubstituted alkenyl groups, substituted and unsubstituted cycloalkyl groups, and unsubstituted ferrocenyl groups;

R$^2$ and R$^3$ are independently selected from the group consisting of substituted and unsubstituted aryl groups, substituted and unsubstituted alkyl groups, substituted and unsubstituted cycloalkyl groups, unsubstituted heterocyclyl groups, and unsubstituted ferrocenyl groups;

R$^4$ is selected from the group consisting of —H, substituted and unsubstituted alkyl groups, substituted and unsubstituted cycloalkyl groups, substituted and unsubstituted aryl groups, trialkylsilyl groups, triarylsilyl groups, alkyldiarylsilyl groups, dialkylarylsilyl groups, —C(=O)—R$^6$ groups, —S(=O)$_2$—R$^6$ groups, —P(=O)R$^6$R$^7$ groups, and —C(=NR$^6$)—R$^7$ groups;

R$^5$ is selected from the group consisting of —H, substituted and unsubstituted alkyl groups, substituted and unsubstituted cycloalkyl groups, substituted and unsubstituted aryl groups, trialkylsilyl groups, triarylsilyl groups, alkyldiarylsilyl groups, dialkylarylsilyl groups, —C(=O)—R$^7$ groups, —S(=O)$_2$—R$^6$ groups, —P(=O)R$^6$R$^7$ groups, and —C(=NR$^6$)—R$^7$ groups;

R$^6$ is selected from the group consisting of substituted and unsubstituted alkyl groups, substituted and unsubstituted alkenyl groups, substituted and unsubstituted cycloalkyl groups, substituted and unsubstituted aryl groups, —OH groups, substituted and unsubstituted alkoxy groups, substituted and unsubstituted aryloxy groups, —NH(alkyl) groups, —NH(aryl) groups, —N(aryl)$_2$ groups, —N(alkyl)$_2$ groups, —N(alkyl)(aryl) groups, —S-alkyl groups, and S-aryl groups;

R$^7$ is selected from the group consisting of substituted and unsubstituted alkyl groups, substituted and unsubstituted alkenyl groups, substituted and unsubstituted cycloalkyl groups, substituted and unsubstituted aryl groups, —OH groups, substituted and unsubstituted alkoxy groups, substituted and unsubstituted aryloxy groups, —NH(alkyl) groups, —NH(aryl) groups, —N(aryl)$_2$ groups, —N(alkyl)$_2$ groups, —N(alkyl)(aryl) groups, —S-alkyl groups, and S-aryl groups;

R$^6$ and R$^7$ may be part of the same alkyl group, alkenyl group, or aryl group such that R$^4$ and R$^5$ together with the two nitrogen atoms of the diazaphosphacycle form a ring; and Y has the formula —(CH$_2$)$_n$— wherein n is 0 and further wherein substituted alkyl groups and substituted alkenyl groups are unsubstituted alkyl groups and unsubstituted alkenyl groups, in which one or more bonds to a carbon or hydrogen is replaced by a bond to a substituent selected from a F, Cl, Br, or I atom in a halide; a O atom in a hydroxyl group, alkoxy group, aryloxy group, ester group, carbonyl group, or carboxyl group; a S atom in a thiol group, alkyl sulfide group, aryl sulfide group, sulfone group, sulfonyl group, or sulfoxide group; a N atom in an amine group, amide group, alkylamine group, dialkylamine group, arylamine group, alkylarylamine group, diarylaimine group, N-oxide group, imide group, enamine group, imine group, oxime group, hydrazone group, or nitrile group; a Si atom in a trialkylsilyl group, dialkylarylsilyl group, alkyldiarylsilyl group, or triarylsilyl group; or a P atom in a phosphine group or phosphoryl group;

substituted cycloalkyl groups are unsubstituted cycloalkyl groups, in which one or more bonds to a carbon or hydrogen is replaced by a bond to a substituent selected from the group consisting of any of the substituents defined above, an unsubstituted alkyl group as defined above, or a substituted alkyl group as defined above; and substituted aryl groups are unsubstituted aryl groups as defined above, in which one or more bonds to a carbon or hydrogen is replaced by a bond to a substituent selected from the group consisting of any of the substituents defined above, an unsubstituted alkyl group as defined above, or a substituted alkyl group as defined above.

2. The method of claim 1, wherein the starting transition metal complex comprises at least one ligand that is replaced by the diazaphosphacycle.

3. The method of claim 2, wherein the at least one ligand that is replaced by the diazaphosphacycle is selected from the group consisting of phosphines, amines, diamines, CO, Cl, Br, nitriles, 1,5-cyclooctadiene, norbornadiene, and other dienes, alkenes, arenes, ketones, alcohols, ethers, thiols, and sulfoxides.

4. The method of claim 1, wherein the diazaphosphacycle has the formula X

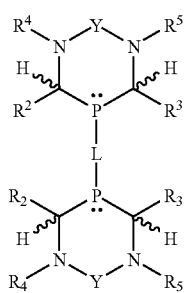

X wherein L is a linking group selected from the group consisting of substituted and unsubstituted alkyl groups, substituted and unsubstituted alkenyl groups, substituted and unsubstituted aryl groups, and unsubstituted ferrocenyl groups.

5. The method of claim 1, wherein the transition metal is selected from the group consisting of Rh, Ru, Pd, Pt, Ir, Ni, Co, and Fe.

6. The method of claim 1, wherein $R^4$ and $R^5$ are both —H.

7. The method of claim 1, wherein $R^4$ is a —C(=O)—$R^6$ group and $R^5$ is a —C(=O)—$R^7$ group.

8. The method of claim 1, wherein, the diazaphosphacycle has the formula IX

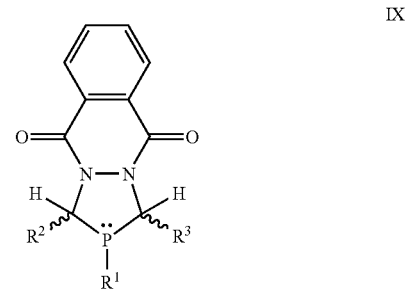

IX wherein the aromatic benzene ring in the diazaphosphacycle of formula IX may be a substituted or unsubstituted aromatic benzene ring, wherein a substituted aromatic benzene ring is an unsubstituted aromatic benzene ring in which one or more bonds to a carbon or hydrogen is replaced by a bond to a substituent selected from the group consisting of any of the substituents defined above, an unsubstituted alkyl group, or a substituted alkyl group as defined above.

9. The method of claim 4, wherein L is selected from the group consisting of ethane, ethylene, propane, benzene, anthracene, 9,10-dihydroanthracene, xanthene, and ferrocene.

10. The method of claim 4, wherein the transition metal is selected from the group consisting of Rh, Ru, Pd, Pt, Ir, Ni, Co, and Fe.

11. The method of claim 4, wherein two of the phosphorus atoms of the diazaphosphacycle are bonded to the transition metal.

* * * * *